(12) United States Patent
Golnaraghi et al.

(10) Patent No.: US 11,457,818 B2
(45) Date of Patent: Oct. 4, 2022

(54) HANDHELD PROBE AND SYSTEM FOR IMAGING HUMAN TISSUE

(71) Applicant: Optican Systems Inc., West Vancouver (CA)

(72) Inventors: Farid Golnaraghi, West Vancouver (CA); Majid Shokoufi, Vancouver (CA)

(73) Assignee: Optican Systems Inc., West Vancouver (CA)

( * ) Notice: Subject to any disclaimer, the term of this patent is extended or adjusted under 35 U.S.C. 154(b) by 289 days.

(21) Appl. No.: 16/479,025

(22) PCT Filed: Jan. 17, 2018

(86) PCT No.: PCT/CA2018/050052
§ 371 (c)(1),
(2) Date: Jul. 18, 2019

(87) PCT Pub. No.: WO2018/132908
PCT Pub. Date: Jul. 26, 2018

(65) Prior Publication Data
US 2019/0328233 A1 Oct. 31, 2019

Related U.S. Application Data

(60) Provisional application No. 62/447,752, filed on Jan. 18, 2017.

(51) Int. Cl.
*A61B 5/00* (2006.01)
*G01N 21/47* (2006.01)
*G01N 21/25* (2006.01)

(52) U.S. Cl.
CPC .......... *A61B 5/0075* (2013.01); *A61B 5/0091* (2013.01); *G01N 21/474* (2013.01);
(Continued)

(58) Field of Classification Search
CPC ............. G01N 21/474; G01N 21/4795; G01N 21/255; A61B 5/0075; A61B 5/0091;
(Continued)

(56) References Cited

U.S. PATENT DOCUMENTS 6,665,557 B1 * 12/2003 Alfano ................ A61B 5/0091
600/473
2006/0111622 A1 5/2006 Merritt et al.
(Continued)

FOREIGN PATENT DOCUMENTS

CA 2417917 A1 2/2002
WO WO0212854 A2 * 2/2002

OTHER PUBLICATIONS

Erickson-Bhatt, Sarah J., et al. "Noninvasive surface imaging of breast cancer in humans using a hand-held optical imager." Biomedical physics & engineering express 1.4 (2015): 045001. (Year: 2015).*
Erickson-Bhatt et al., "Noninvasive Surface Imaging of Breast Cancer in Humans using a Hand-held Optical Imager", Biomedical Physics & Engineering Express, vol. 1, No. 4, Oct. 2015, pp. 045001 [See Supplementary European Search Report].
(Continued)

*Primary Examiner* — Dominic J Bologna
(74) *Attorney, Agent, or Firm* — FisherBroyles LLP; Kevin D. Jablonski

(57) ABSTRACT

A diffuse-optical-spectroscopy system and method for scanning human tissue. The system includes: (a) a handheld probe operable to emit electromagnetic radiation at one or more wavelengths corresponding to absorption associated with one or more human-tissue constituents, respectively, the handheld probe being operable to detect received electromagnetic radiation at each of the wavelengths; and (b) a processor operable to produce, in response to the received electromagnetic radiation, one or more cross-sectional images of the human tissue respectively associated with the wavelengths. The handheld probe includes first and second sources for emitting the electromagnetic radiation and one or more sensors for detecting the received electromagnetic radiation. The sensors are aligned along a first axis and face in an outward direction. The first and second sources are aligned along the first axis, face in the outward direction, and are disposed on either side of the sensors.

7 Claims, 29 Drawing Sheets

(52) U.S. Cl.
CPC ....... *G01N 21/4795* (2013.01); *G01N 21/255* (2013.01); *G01N 2201/0221* (2013.01); *G01N 2201/0627* (2013.01)

(58) Field of Classification Search
CPC ...... A61B 2562/043; A61B 2560/0431; G01B 2201/0221; G01B 2201/0627
See application file for complete search history.

(56) References Cited

U.S. PATENT DOCUMENTS

| | | | | |
|---|---|---|---|---|
| 2006/0122475 | A1* | 6/2006 | Balberg | A61B 5/1464 600/323 |
| 2013/0256534 | A1* | 10/2013 | Micheels | G01N 21/255 250/339.07 |
| 2014/0243681 | A1* | 8/2014 | Hielscher | A61B 5/6807 600/473 |
| 2017/0195589 | A1* | 7/2017 | Kovacovsky | G01S 17/89 |

OTHER PUBLICATIONS

Erickson et al., "Hand-held based near-infrared optical imaging devices: A review", Medical Engineering & Physics, Butterworth-Heinemann, vol. 31, No. 5, Jun. 2009, pp. 495-509 [See Supplementary European Search Report].

Xu el al., "A Prospective Pilot Clinical Trial Evaluating the utility of a Dynamic Near-infrared Imaging Device for Characterizing Suspicious Breast Lesions", Breast Cancer Research, Current Medicine Group Ltd.. vol. 9, No. 6, Dec. 2007, p. R88 [See Supplementary European Search Report].

Supplementary European Search Report issued in European Patent Application No. 18 74 1716 dated Sep. 25, 2020.

Shokoufi et al., "Development of a Handheld Diffuse Optical Breast Cancer Assessment Probe", Journal of Innovative Optical Health Sciences, vol. 9, No. 2, Oct. 30, 2015, pp. 1650007-1 to 1650007-10 See International Search.

* cited by examiner

HANDHELD PROBE AND SYSTEM FOR IMAGING HUMAN TISSUE

BACKGROUND OF THE INVENTION

1. Field of Invention

This invention relates to diffusion optical spectroscopy and, in particular, to a handheld probe and system using the handheld probe for cross-sectional imaging of human tissue.

2. Description of Related Art

According to the Canadian and American cancer societies' reports, breast cancer is the most common cancer in women and it is ranked as the second cause of death, in North America. Breast cancer affects approximately one in eight North America women during their lifetime. Treatment entails a number of steps from the time of diagnoses to a consistent follow-up after the treatment stage. These steps have to be taken seriously if there is any suspicions lesion. Introducing new technology or improving one or more of the assessment parameters including: accuracy, sensitivity, specificity or positive predictive value on current techniques, may help physicians to detect breast cancer in its early stage, which is crucial in women's health. The screening methods of clinical breast exam (CBE) and X-ray mammography are questionable for their lower sensitivity. X-ray mammography is a preliminary screening methodology, it is painful and uses harmful ionizing X-ray radiation.

Ultrasound, x-ray mammography, and magnetic resonance imaging (MRI) are commonly used for breast cancer detection where X-ray mammography is the primary screening technique for breast cancer. Although X-ray mammography is the principle modality for breast cancer screening, it is recommended for women over the age of 50, because it has low sensitivity (67.8%) for younger women or women with dense breasts. In addition, it has a potential health risk as an effect of ionizing radiations. Therefore, because of X-ray mammography's limitations, researchers have been encouraged to use different breast cancer detection modalities, such as diffuse optical tomography, impedance spectroscopy and elasto-graphy.

Over the past three decades great progress has occurred in optoelectronics components and fiber optics. In parallel with these developments, near-infrared (NIR) optical imaging, in association with optoelectronic devices and fiber optics, also have been developed very rapidly and currently NIR optical imaging approaches have been advanced for breast cancer diagnosis. This technique is known as a noninvasive and promising method for compositional and functional imaging of extremely scattering mediums, such as brain and breast.

The optical properties of the breast tissue have been widely studied. For example, it is known that the absorption of the four main constituents of breast tissue, namely water, fat, deoxyhemoglobin (Hb) and oxyhemoglobin ($HbO_2$), is low in the wavelength spectrum from 650 nm to 1100 nm, which allows light to travel deeply into the breast tissue.

A number of handheld diffuse optical probes have been implemented and tested for breast cancer detection and screening. Almost all of the probes are designed in reflectance geometry to measure optical properties of the breast tissue underneath of the probes. Laser light sources or fiber coupled laser light sources in near infrared range are used to determine the concentration of main chromophores in the breast tissue related to sensing anomalies. However, laser and fiber-optic based illumination techniques are complex, large in size and costly.

An object of the invention is to address the above shortcomings.

SUMMARY

The above shortcomings may be addressed by providing, in accordance with one aspect of the invention, a diffuse-optical-spectroscopy system for scanning human tissue. The system includes: (a) a handheld probe operable to emit electromagnetic radiation at one or more wavelengths corresponding to absorption associated with one or more human-tissue constituents, respectively, the handheld probe being operable to detect received electromagnetic radiation at each of the one or more wavelengths; and (b) a processor operable to produce, in response to the received electromagnetic radiation, one or more cross-sectional images of the human tissue respectively associated with the one or more wavelengths.

The handheld probe may include one or more sensors for detecting the received electromagnetic radiation, the one or more sensors being aligned along a first axis and facing in an outward direction. The handheld probe may include first and second sources for emitting the electromagnetic radiation, the first and second sources being aligned along the first axis, facing in the outward direction, and disposed on either side of the one or more sensors. The one or more wavelengths may include at least four wavelengths corresponding to absorption associated with at least four human-tissue constituents. Each of the at least four wavelengths may be in at least one of a visible region, a near-infrared region, and an infrared region of the electromagnetic spectrum. The at least four human-tissue constituents may include deoxyhemoglobin, oxyhemoglobin, water and fat. Each of the first and second sources may include first, second, third and fourth light sources operable to emit the electromagnetic radiation at first, second, third and fourth wavelengths, respectively, each of the first, second, third and fourth light sources being selected from the group consisting of a light-emitting diode, an encapsulated light-emitting diode, and a laser. The handheld probe may include a linear array detector (charge-coupled device or linear photodiode) that includes the one or more sensors. The electromagnetic radiation may be continuous wave electromagnetic radiation.

In accordance with another aspect of the invention, there is provided a method of scanning human tissue by diffuse-optical-spectroscopy. The method involves: (a) emitting electromagnetic radiation at one or more wavelengths corresponding to absorption associated with one or more human-tissue constituents, respectively, by a handheld probe placed in proximity to the human tissue; (b) detecting by the handheld probe received electromagnetic radiation at each of the one or more wavelengths; and (c) in response to the received electromagnetic radiation, producing by a processor one or more cross-sectional images of the human tissue respectively associated with the one or more wavelengths.

Step (b) of the method may involve detecting the received electromagnetic radiation by one or more sensors of the handheld probe when the one or more sensors are aligned along a first axis and facing in an outward direction. Step (a) of the method may involve emitting the electromagnetic radiation by first and second sources of the handheld probe when the first and second sources are aligned along the first axis, facing in the outward direction, and disposed on either side of the one or more sensors. Step (a) of the method may involve emitting the electromagnetic radiation at the one or more wavelengths that may include at least four wavelengths corresponding to absorption associated with at least four human-tissue constituents, each of the at least four wavelengths being in at least one of a visible region, a near-infrared region, and an infrared region of the electromagnetic spectrum, the at least four human-tissue constituents comprising deoxyhemoglobin, oxyhemoglobin, water and fat. Step (a) of the method may involve emitting the electromagnetic radiation by first, second, third and fourth light sources at first, second, third and fourth wavelengths, respectively when each of the first, second, third and fourth light sources are selected from the group consisting of a light-emitting diode, an encapsulated light-emitting diode, and a laser. Step (b) of the method may involve detecting the received electromagnetic radiation by at least one of a charge-coupled device and an array photodiode of the handheld probe when the at least one of a charge-coupled device and an array photodiode comprises the one or more sensors. Step (a) of the method may involve emitting continuous wave electromagnetic radiation.

In accordance with another aspect of the invention, there is provided a system for scanning human tissue by diffuse-optical-spectroscopy. The system includes: (a) source means for emitting electromagnetic radiation at one or more wavelengths corresponding to absorption associated with one or more human-tissue constituents, respectively; (b) receiving means for detecting received electromagnetic radiation at each of the one or more wavelengths; and (c) processing means for producing, in response to the received electromagnetic radiation, one or more cross-sectional images of the human tissue respectively associated with the one or more wavelengths.

Diffuse optical spectroscopy (DOS) and diffuse optical Imaging (DOI) are methods for breast cancer diagnosis which are noninvasive and nonionizing techniques. The DOB-Scan probe is used to measure optical properties of breast tissue and create functional and compositional cross-sectional images of the breast. Four wavelengths light emitting diodes (LED), encapsulated in a package (eLED), are used to illuminate the breast tissue. A linear charge coupled device (CCD) measures the intensity of the scattered photons at different radial destinations from the illumination source on the surface of the breast tissue. The proposed method replaces fiber optic based illumination techniques, which increases the complexity, size and cost of a potential probe, by multi-wavelengths eLED which acts as a pencil beam source in such a scattering media like the breast tissue. In addition, the DOB-Scan probe and associated algorithm can create cross-sectional images of the breast tissue underneath of the probe by using high resolution linear CCD. The introduced technique miniaturizes the probe, while maintaining reliability and accuracy of this technique in breast imaging. Multi-wavelength light sources are used to increase the capability of the probe by creating separate images for four primary chromophores of the breast tissue including deoxyhemoglobin, oxyhemoglobin, fat and water. The average scattering coefficient of the medium and localized concentration variations in oxyhemoglobin and deoxyhemoglobin can be measured utilizing the probe. In order to evaluate the performance of DOB-Scan probe, a series of tissue-like materials (phantoms), containing of Intralipid®, Black ink, Delrin®, and Pierce™ have been used to produce the experimental results indicated below. The test results provide evidence that the DOB-Scan probe can detect any inhomogeneity inside the phantoms.

The foregoing summary is illustrative only and is not intended to be in any way limiting. Other aspects and features of the present invention will become apparent to those of ordinary skill in the art upon review of the following description of embodiments of the invention in conjunction with the accompanying figures and claims.

BRIEF DESCRIPTION OF THE DRAWINGS

In drawings which illustrate by way of example only embodiments of the invention.

DETAILED DESCRIPTION

A system for scanning human tissue by diffuse-optical-spectroscopy includes: (a) source means for emitting electromagnetic radiation at one or more wavelengths corresponding to absorption associated with one or more human-tissue constituents, respectively; (b) receiving means for detecting received electromagnetic radiation at each of the one or more wavelengths; and (c) processing means for producing, in response to the received electromagnetic radiation, one or more cross-sectional images of the human tissue respectively associated with the one or more wavelengths.

Figure 5:
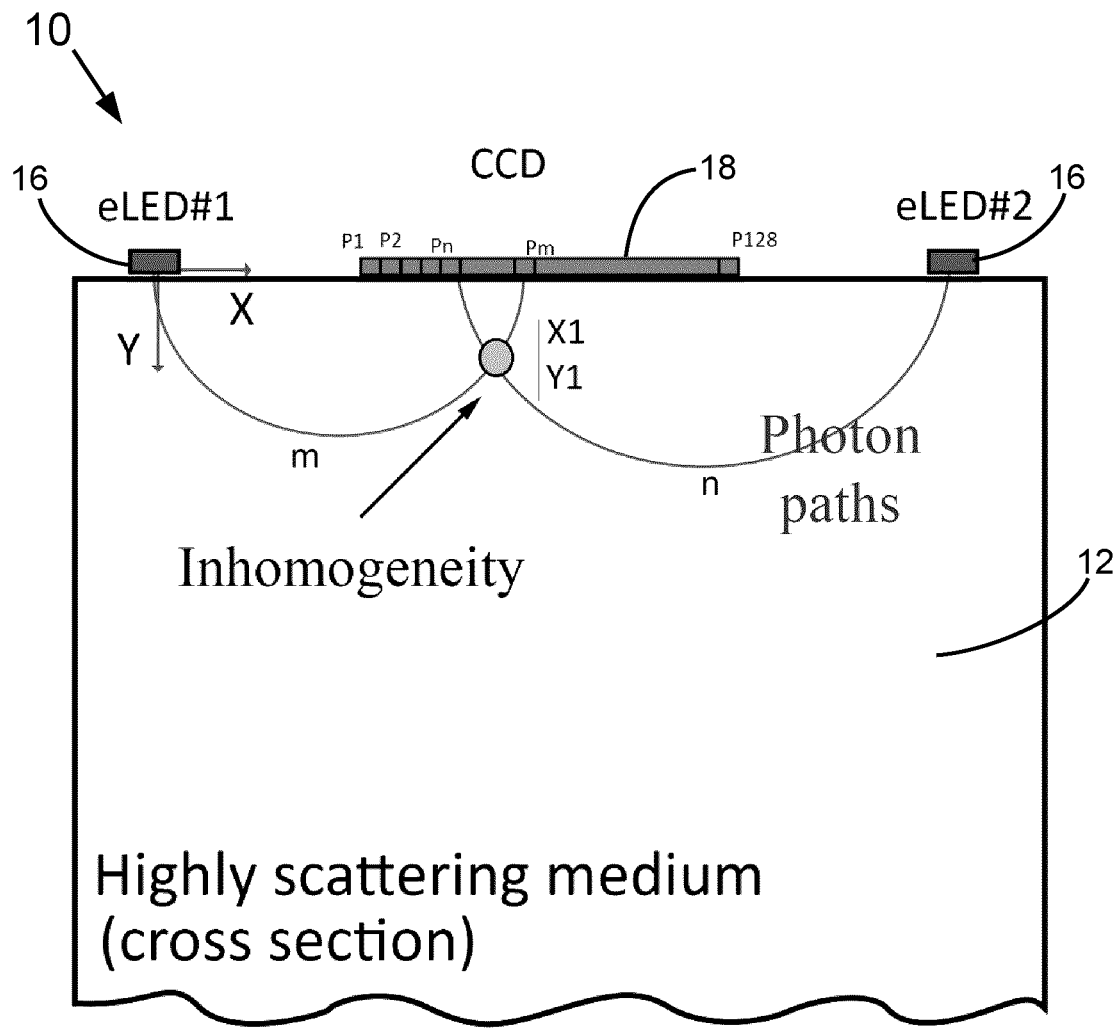
FIG. 5 is a schematic representation of the handheld probe shown in FIG. 1, showing a highly scattering medium.

With reference to the Figures, a handheld diffuse optical breast scanning probe, an exemplary prototype of which is variously referred to herein as the probe and/or the DOB-Scan probe 10, is operable for functional and compositional cross-sectional imaging of breast tissue 12 (FIG. 5). In order to evaluate performance and usability of the device, the DOB-Scan probe 10 is tested on breast tissue-mimicking phantoms 14 (FIGS. 6, 7a, 7b and 7c) which have similar optical properties of breast tissue 12 and, thereafter, tested on human subjects. The DOB-Scan probe uses single-wavelength or multi-wavelengths light emitting diode(s) (LED), encapsulated light emitting diode(s) (eLED) 16, and/or laser(s) as an illumination source containing one or more visible, near infrared, and/or infrared wavelengths such as four near infrared wavelengths, 690 nm, 750 nm, 800 nm, and 850 nm. In one embodiment, LEDs of each eLED 16 are set 0.5 mm apart from each other (within the eLED 16) and perform as a multi-wavelengths pointed illumination source in such a scattering medium. A linear charge coupled device (CCD) 18, linear array photodiode(s), and/or a photodiode-array detector of the DOB-Scan probe 10 is used to measure the intensity of the scattered photons, in a line with 2048 points, on the surface of the breast 12 (or phantom 14) to create functional and cross-sectional images of the breast tissue 12 underneath of the DOB-Scan probe 10. The illumination source wavelengths are chosen to correspond to wavelengths for which the breast fat has lowest absorption.

Figure 1:
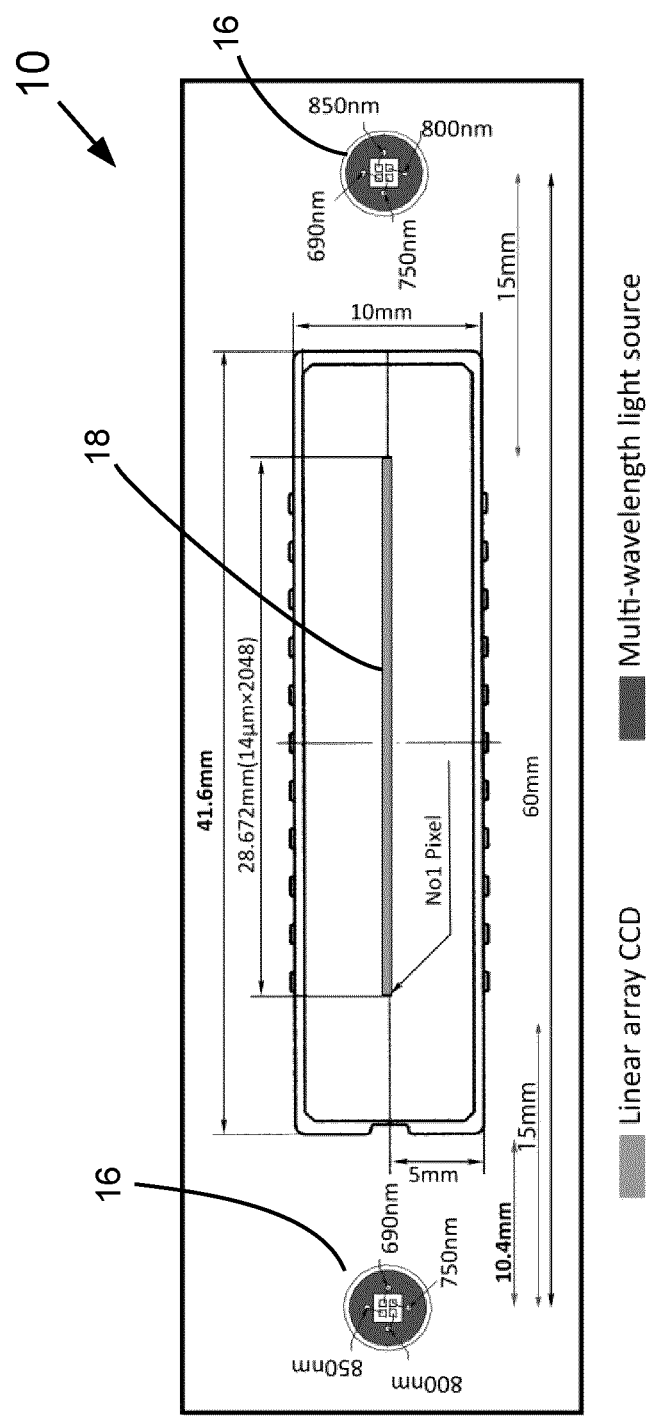
FIG. 1 is a schematic representation of a handheld probe according to a first embodiment of the invention, showing sources and a detector.
Figure 2:
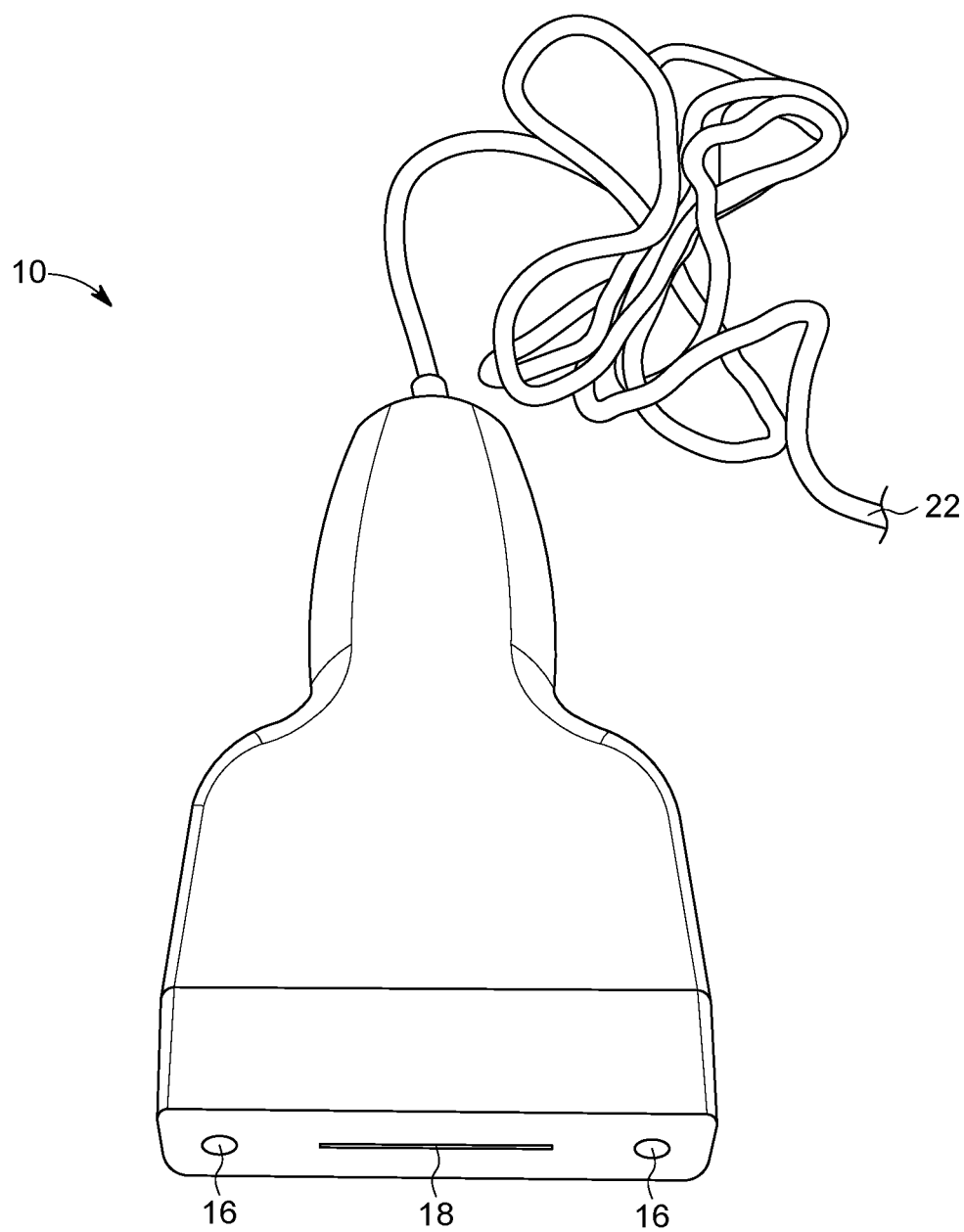
FIG. 2 is a photograph of the prototypical handheld probe shown in FIG. 1, showing locations of first and second eLEDs and a linear CCD.

The DOB-Scan probe 10 is used to create two-dimensional cross-sectional images of breast tissue 12 in-vivo. In the probe, an array detector (e.g. CCD 18) is used to create cross-sectional images of breast tissue 12. The breast tissue 12 is illuminated with two eLEDs 16 which in an exemplary embodiment are located 60 mm away from each other (15 mm away from either side of the CCD 18) and are used to have symmetrical light illumination sources. FIGS. 1 and 2 present a sketch and photograph of the DOB-Scan probe 10, respectively. As it is illustrated in FIG. 1 and FIG. 2, the linear CCD 18 and light illumination sources (e.g. eLEDs 16) are located in reflectance geometry. The diffusion of light in the selected wavelengths are maximum due to minimum absorption of breast fat.

An exemplary embodiment of the DOB-Scan probe 10 for functional and compositional cross-sectional imaging of the breast tissue 12 employs multi-wavelength diffuse optical spectroscopy technique with four wavelengths encapsulated in an eLED 16 light source in the near infrared spectrum range. The device and associated system hardware provide four two-dimensional images of the breast tissue's function and composition. Each eLED 16 contains four wavelengths (e.g. 690 nm, 750 nm, 800 nm and 850 nm), which are illuminated into the breast tissue 12 once a time and the linear CCD 18 collects scattered light on the skin of the breast tissue 12. Then, the system processes the data and transfers them to a host computer 20 for further analysis and image reconstruction. From the collected data at one or more (e.g. four) different wavelengths, the system is able to create one or more cross-sectional optical absorption images for concentration of one or more different chromophores in the breast tissue such as Hb and $HbO_2$ which are markers for cancerous tissue. Also, the prototypical probe and method accurately create cross-sectional optical absorption images such that there is no need to use laser diodes or fiber coupled laser diodes as an illumination source, although such illumination sources may be employed in variations of embodiments of the present invention. Real time data acquisition system components add functional imaging advantages to the probe. In the exemplary prototypical embodiment, the image reconstruction for each wavelength is performed at the rate of 24 Hz which is sufficient for functional imaging of biological activity.

Figure 3:
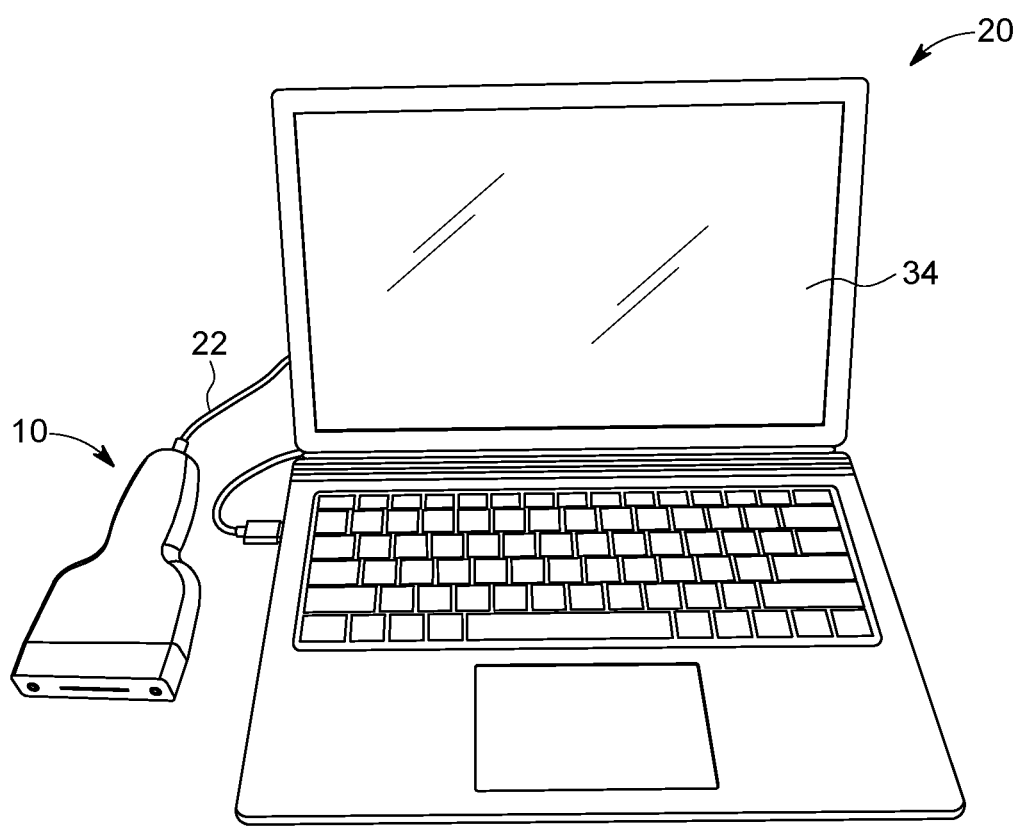
FIG. 3 is a photograph of a prototypical system according to the first embodiment, showing the prototypical handheld probe connected to a host computer.

A photograph of the DOB-Scan probe 10 prototype with its system hardware housed within the DOB-Scan probe 10 is shown in FIG. 3. In variations of embodiments, one or more system components may be housed externally to the DOB-Scan probe 10. The host computer 20 includes a processor and memory in a manner known in the art. While FIG. 3 shows a wired connection 22 between the DOB-Scan probe 10 and the host computer 20, in some embodiments the DOB-Scan probe 10 is battery-powered and operable to communicate with the host computer 20 by any suitable wireless communications technology (e.g. Bluetooth™ or Wi-Fi).

Figure 4:
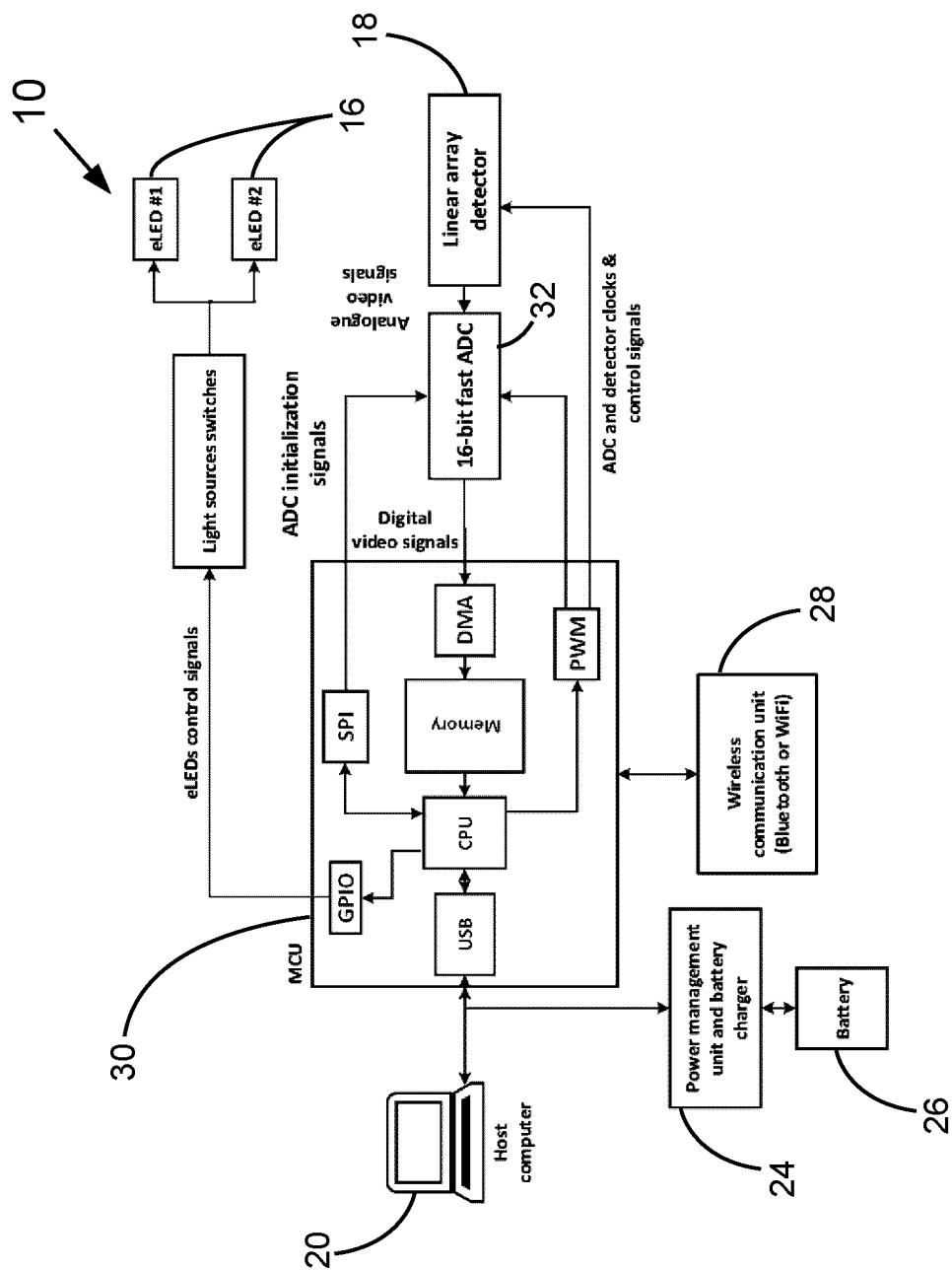
FIG. 4 is a schematic representation of the system shown in FIG. 3, showing a wireless communication unit.

Eight near infrared light sources are used to illuminate the breast tissue 12 through two eLEDs 16. A Schematic diagram of the instrument is shown in FIG. 4, including showing a power management unit and battery charger 24, a battery 26, and a wireless communication unit 28. The wireless communication unit 28 may implement Bluetooth™, Wi-Fi and/or other wireless communications technology for example. Each wavelength is illuminated in the breast tissue 12 once a time and the linear CCD 18 collects scattered light on the skin of the breast tissue and converts it to analogue voltage. Then, analog signals are converted to digital signals and passed to the main processor. The microcontroller unit (MCU) 30 is responsible to create control signals for illumination sources (e.g. eLEDs 16), analog to digital convertor (ADC) 32 and CCD 18. The MCU 30 reads digital data from ADC 32 and transfers data to host computer 20 for further analysis, as well.

Two eLEDs 16 (e.g. from Marubeni America Corporation L690/750/800/850) are used in the probe 10, which are located 15 mm away from each end-side of the detector (e.g. CCD 18) as shown in FIG. 1. Each eLED 16 includes four wavelengths: 690 nm, 750 nm, 800 nm and 850 nm. Penetrations of photons in these wavelengths are maximized due to low absorption of breast fat at the chosen wavelengths. In total, the probe has eight LEDs which can turn on and off individually or sequentially by the time period of 200 milliseconds. Intensity of each LED can be calibrated by trimmer potentiometer on the instrument (e.g. DOB-Scan probe 10).

The light detector plays an important role in the instrument. In order to have high resolution images, it should have large number of light sensors with small size and patches. The light sources are located at two ends of the detector and the illuminated photons are travelling in different path lengths to reach to the photodetectors. The photodetectors which are located close to the active light source will be exposed to a higher light intensity and the ones that are placed far from active light source, will receive lower light intensity. Therefore, the photodetectors must have a large dynamic range to allow measurement for both small and large source-photodetector separations. The photodetector circuit of the prototype is specially designed to address these challenges. The light detector (ILX511, SONY™) used for the probe 10 is a linear charge coupled device 18, which has a fixed capacitor associated with each photodetector (pixel). The photodetector chip of the prototype has 2086 pixels in total which is called one frame. 32 pixels at the beginning of the frame and 6 pixels at the end of the frame are dummy pixels. Therefore, the photodetector of the prototype has 2048 effective pixels with 14 μm pixel pitch; consequently the effective imaging area of the prototype is 28.672 mm (2048×14 μm).

NIR photons migration in biological tissue and optical properties of the breast tissue are compatible with diffusion optical spectroscopy. Four main absorbers in the breast tissue in NIR range (650 nm to 1100 nm) are deoxyhemoglobin (Hb), oxyhemoglobin ($HbO_2$), water and fat. The optical properties of the breast tissue are widely studied and published in academic journal articles. These studies demonstrate that absorption of water and fat are low in NIR range, which allows photons to travel deeply into the breast tissue.

The raw data acquired from the linear CCD 18 (2048 pixels, pixels pitch: 14 μm), two light sources and four NIR wavelengths are one frame which obtained from surface of the breast tissue. Therefore, total numbers of measurement points for one frame scan are 16384 (2048×2×4). The propagation of the light in a highly scattering medium like the breast tissue 12 can be precisely modeled utilising the diffusion equation. As illustrated in FIG. 1, source-detector separations in the DOB-Scan probe 10 vary from 15 mm to 43.672 mm. Therefore, illuminated light into the breast tissue pass different depth and path in the breast tissue to reach to the detectors. The measured photons travel longer path and deeper in the breast tissue 12 while source-detector separation is wider. In order to calculate absorption coefficient ($\mu_a$) of the paths photons travel in the breast tissue 12, a closed form solution for the diffusion equation in a semi-infinite homogeneous medium may be employed while light source and detector are located in spatially reflectance geometry. The extracted absorption coefficients for photon paths are used to create two-dimensional cross-sectional image for each NIR wavelengths.

In particular, in a highly scattering medium such as breast tissue 12, the radiative transfer equation can be simplified by the diffusion equation as follows:

$$\nabla D(r) \nabla \Phi_d(r) - \mu_a c_m \Phi_d(r) = -S(r) \quad (1)$$

where $\Phi_d$ represents the intensity at the detector located r mm away from the illumination source(S(r)). $c_m$ and $\mu_a$ are the photons velocity in the medium and absorption coefficient, respectively. D represents diffusion coefficient.

Within the NIR spectrum range (650 nm to 1100 nm), the photons' migration in the biological tissue is in the scattering region and diffusion equation can be used to describe photons propagation. The following expression (2) presents analytical solution for the diffusion equation in a homogeneous media while the illumination source and detector setting in reflectance geometry.

$$R(d) = \frac{1}{4\pi\mu_t'}\left[\left(\mu_{\mathit{eff}} + \frac{1}{r_1}\right)\frac{\exp(-\mu_{\mathit{eff}} r_1)}{r_1^2} + \left(\frac{4}{3}A+1\right)\left(\mu_{\mathit{eff}} + \frac{1}{r_2}\right)\frac{\exp(-\mu_{\mathit{eff}} r_2)}{r_2^2}\right] \quad (2)$$

$$r_1 = \sqrt{\left(\frac{1}{\mu_t'}\right)^2 + d^2}, \; r_2 = \sqrt{\left(\frac{\left(\frac{4}{3}\right)A+1}{\mu_t'}\right)^2 + d^2},$$

$$\mu_{\mathit{eff}} = \sqrt{3\mu_a\mu_t'}, \; \mu_t' = \mu_a + \mu_s' = \mu_a + (1-g)\mu_s$$

Where the parameters are defined as follows:
$\mu_a$ Absorption coefficient
$\mu_s$ Scattering coefficient
$\mu_s'$ Reduced scattering coefficient
$\mu_{\mathit{eff}}$ Effective attenuation coefficient
$\mu_t$ Total attenuation coefficient
R(d) Measured scattered photon intensity at the distance of d from illumination source
A Internal reflection parameter The diffusion equation is effective while r is greater than $10\times(\mu_a+\mu_s')^{-1}$ and $\mu_a<<\mu_s'$;

There are several studies demonstrating that there is not remarkable changes on the total attenuation coefficient ($\mu_t'$) of normal and cancerous breast tissue. Because, $\mu_a$ of the breast tissue is much smaller than $\mu_s'$, so fluctuation in $\mu_a$ will not have remarkable variation on $\mu_t'$. These studies demonstrate that $\mu_a$ and $\mu_s'$ of the breast tissue are in the range of 0.002 mm$^{-1}$ to 0.012 mm$^{-1}$ and 0.6 mm$^{-1}$ to 1.5 mm$^{-1}$, respectively, at the NIR spectrum range. It has also been shown that variation on $\mu_t'$ does not have notable results on the back scattered photons at the photodetector position.

Oxy-hemoglobin (HbO$_2$), deoxy-hemoglobin (Hb), water (H$_2$O), and fat are the four primary chromophores in the breast tissue which contribute to the attenuation at wavelength $\lambda$ and concentration of HbO$_2$ and Hb vary by the time. The direct-approach-method equation (3) can be used to create cross-sectional images for the four chromophores concentration and concentration variations in Hb ($\Delta$cHb) and HbO$_2$ ($\Delta$cHbO$_2$) shown in the cross-sectional images.

$$\mu_a(\lambda) = \sum_n \varepsilon_n^\lambda \times C_n, \quad (3)$$

n = fat, water, HbO$_2$ and Hb $\lambda$ = 690 nm, 750 nm, 800 nm and 850 nm

Where $\varepsilon_n^\lambda$ is the molar absorption extinction coefficient for the chromophore type n (n should be Hb, HbO$_2$, H$_2$O and Fat) at illuminated wavelength of $\lambda$ (690 nm, 750 nm, 800 nm, 850 nm) and C$_n$ is the total concentration of the chromophore in the photons path lengths. While the exemplary wavelengths of 690, 750, 800 and 850 nm are mentioned herein in association with the chromophores of Hb, HbO$_2$, H$_2$O and Fat, it is understood that each of the wavelengths may vary in any range that is suitably associated with a corresponding chromophore or other human-tissue constituent or type.

In the wider source-detector separation, back scattered light travels through deeper and longer paths in the tissue. Concentrations of Hb and HbO$_2$ vary by the heartbeat. Concentration distribution of four absorbers can be calculated by solving equation (3) for different light paths to reconstruct images for the absorbers and visualize the variation of them in the breast tissue.

The obtained raw data from the exemplary prototype having 2048 pixels, 2 sources and 4 wavelengths are measurement points collected from surface of the tissue. A reconstruction algorithm is useful for converting the surface measured light intensity into two-dimensional cross-sectional images of the chromophores. In the first step, the absorption coefficient ($\mu_a$) of each light paths are calculated by utilizing equation (2) while the tissue is illuminated by each wavelength. In order to reduce effect of the noise on the measurements, we reduced the number of measurement points to 128 points (P1 to P128) by averaging 16 pixels. It can be assumed that the origin of the coordinate is located on the center of light source #1 as showed in FIG. 5. As mentioned earlier, two sets of the data are collected for each wavelength: 1) while eLED #1 12 is on, 2) while eLED #2 12 is on. Assume we want to calculate the total absorption coefficient in location (X1, Y1) as shown in FIG. 5. The illuminated light from eLED #1 12 travels along the path m and reaches to the CCD 14, and then intensity of scattered light is measured by the m$^{th}$ pixel of the CCD 14. A similar process occurs while eLED #2 12 is on. The illuminated light from eLED #2 12 travels along the path n and reaches to the CCD 14 and scattered light is measured by n$^{th}$ pixel of the CCD 14. Then the absorption coefficient at (X1, Y1) is calculated as a superposition of two light path lengths of illuminated light from eLED #1 12 and eLED #2 12.

Table 1 presents a brief specification of the exemplary DOB-Scan probe in prototype form.

TABLE 1

DOB-Scan Probe characteristics and parameter

| Parameter | Value |
| --- | --- |
| Wavelength | 2 × (690 nm, 750 nm, 800 nm, 850 nm) |
| Detector type | Linear CCD |
| Detector resolution | 2048 pixels |
| Image resolution | 128 × 128 pixels |
| Image length | 28.67 mm |
| Image depth | 24 mm |
| Detector sensitivity | 1800 (V/Lx.S)@660 nm |
| Illumination tech. | Continuous wave |
| Max. frame rate | 24 |
| Power consumption | 100 mA @ 5 V |

A MATLAB® (MATLAB R2012b, MathWoks®) based software interface gives the user complete controls of the hardware in addition to allowing them to collect, store, analyze data and create images, including color-mapped images, on the host computer. The software interface communicates with the DOB-Scan probe 10 via USB2.0 (or other serial communications technology) virtual comport and contains a graphical user interface (GUI) 34, as shown in FIG. 3, for operator's ease of use. The GUI 34 is comprised of a series of tabs and collected data graphs, which are used for various operations including: Manual and periodic light source selection, CCD 18 integration time setting and data collection. Upon launching the software interface the user must select illuminated wavelengths manually or set it periodically in LEDs control panel. In the manual mode 24 frames per second are collected from the image sensor, which it is sufficient for functional imaging of biological tissue. In periodic mode each wavelength is illuminated for 200 milliseconds and the data are collected with the same period. In this mode, eight frames are collected sequentially while different wavelengths are illuminated into the biological tissue, and in order to measure ambient light effect on the image sensor, one more frame is collected while all the LEDs are turned off.

Experimental Results

Figure 6:
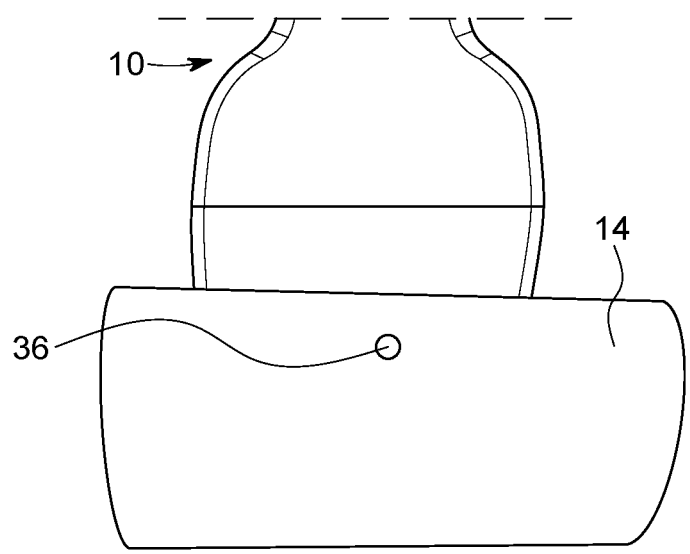
FIG. 6 is a photograph of a breast phantom for use in testing the prototypical system shown in FIG. 3, showing a hole in the breast phantom for containing liquid providing a phantom representation of a cancerous tumor.

To verify performance of the exemplary prototype of the designed DOB-Scan probe 10, a study based upon tissue equivalent material was conducted. In this study, we used an incomplete (truncated) cylindrical shaped (8 cm diameter and 28 cm length) acetal resin rod 14 (Delrin®) and Intralipid® to mimic background breast tissue 12 due to similarity in optical properties to the breast fat. ($\mu_s'$=2.3 mm$^{-1}$ and $\mu_a$=0.002 mm$^{-1}$). Also, optical properties of these two materials are well-documented and known. In order to mimic cancerous lesions, a 5 mm hole 36 is placed on the side wall of the cylinder 14; located 15 mm below the incomplete side of the Acetal resin rod 14, as shown in FIG. 6, which is filled with tumor-like liquid phantom. A solution of Infralipid® 20% emulsion (Fresenius Kabi Inc.), water and black ink (Higgins India ink) is used to mimic breast tumor in the background phantom 14. Black India ink is used in this study as an absorber for its flat absorption in the NIR spectrum range and it has water-solubility properties.

Figure 7A:
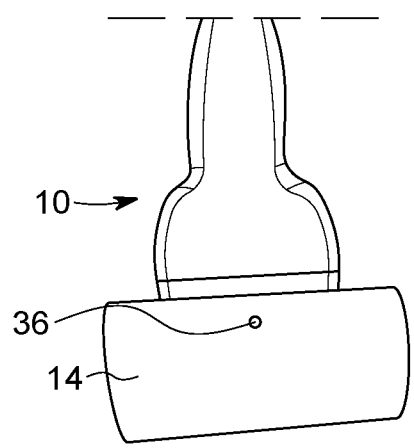
FIG. 7a is a photograph of the breast phantom of FIG. 6 and the prototypical system of FIG. 3, showing the prototypical handheld probe's middle placed along the center of the hole of the breast phantom containing India black ink.
Figure 7B:
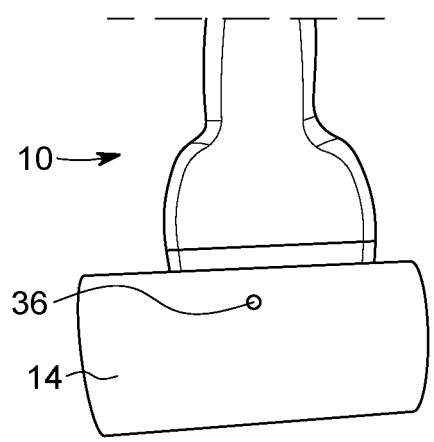
FIG. 7b is a photograph of the breast phantom of FIG. 6 and the prototypical system of FIG. 3, showing the prototypical handheld probe's middle placed to the left of the hole of the breast phantom containing India black ink.
Figure 7C:
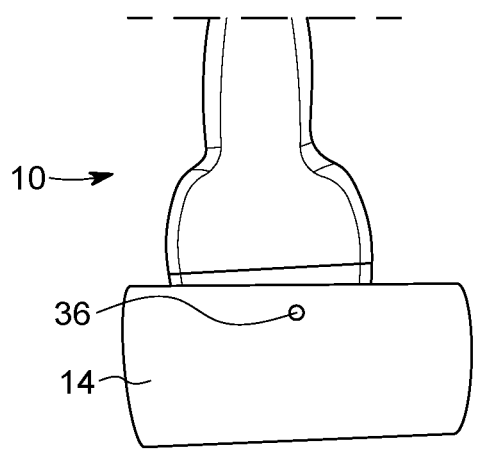
FIG. 7c is a photograph of the breast phantom of FIG. 6 and the prototypical system of FIG. 3, showing the prototypical handheld probe's middle placed to the right of the hole of the breast phantom containing India black ink.

In the first experiment, we used phantom #1 14 in which the hole 36 was filled with tumor-like liquid phantom. The liquid-phantom is a solution consisting of 1 L water, 50 mL Intralipid® and 1.5 mL India black ink. In this case, we put the probe 10 in three different locations on the phantom 14 in which the middle line of the probe 10 (middle of the CCD 18) is aligned: a) along the center of the hole 36, b) 7 mm to the left of the hole 36 center, and c) 7 mm to the right of the hole 36 center, as shown in FIGS. 7a, 7b, and 7c, respectively.

Figure 8A:
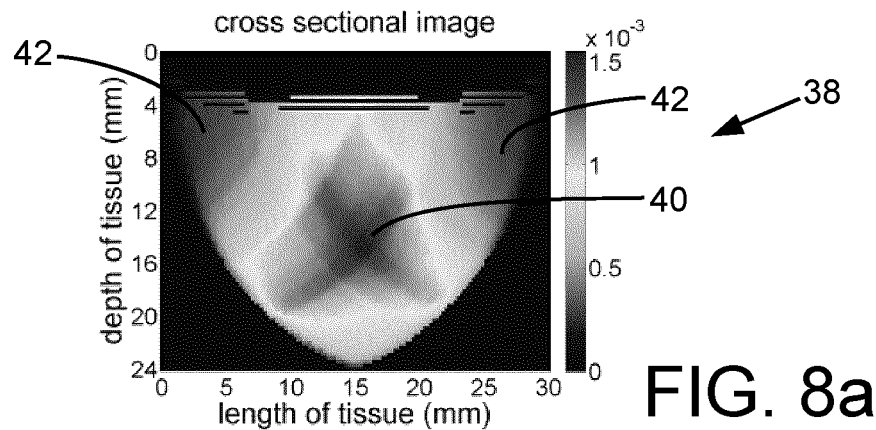
FIG. 8a is a cross-sectional image produced by the prototypical system shown in FIG. 3 when the probe is emitting electromagnetic radiation at 690 nm and is located along the center of the breast phantom's hole containing India black ink.
Figure 8B:
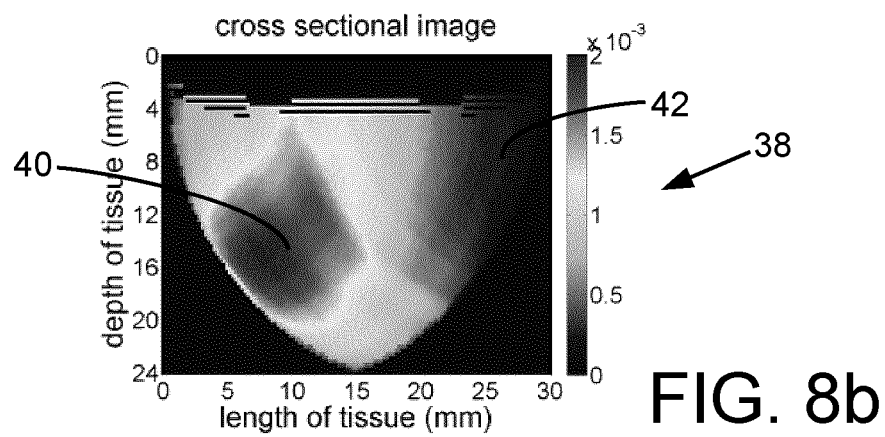
FIG. 8b is a cross-sectional image produced by the prototypical system shown in FIG. 3 when the probe is emitting electromagnetic radiation at 690 nm and is located to the left of the breast phantom's hole containing India black ink.
Figure 8C:
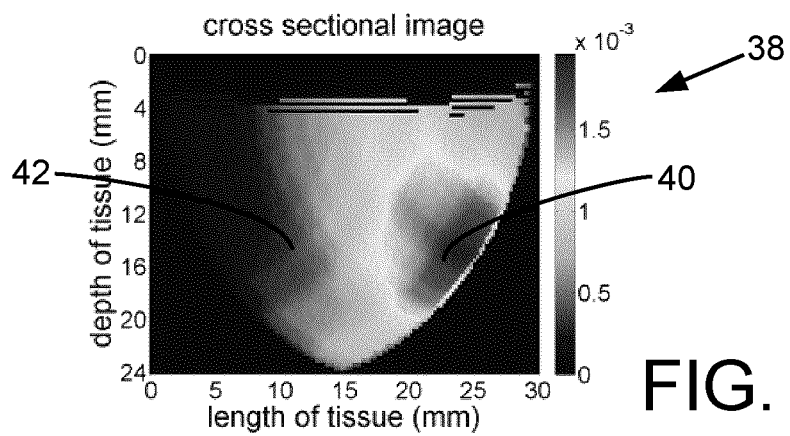
FIG. 8c is a cross-sectional image produced by the prototypical system shown in FIG. 3 when the probe is emitting electromagnetic radiation at 690 nm and is located to the right of the breast phantom's hole containing India black ink.

FIGS. 8a, 8b, and 8c show the reconstructed cross-sectional images 38 of the phantom for the wavelength of 690 nm while the breast phantom's hole 36 contains the India black ink solution and while the probe 10 is located: a) along the center of the hole 36, b) 7 mm to the left of the hole 36 center, and c) 7 mm to the right of the hole 36 center. The reddish area 40 on the images shows the location of the hole 36 on the phantom, in contrast to differently colored areas such as the non-reddish area(s) 42. Since, black India ink has flat absorption spectrum in the NIR range, we have similar images for all wavelengths (690 nm, 750 nm, 800 nm and 850 nm). The test results demonstrate that the probe 10 can capture any inhomogeneity in the phantom.

Figure 9A:
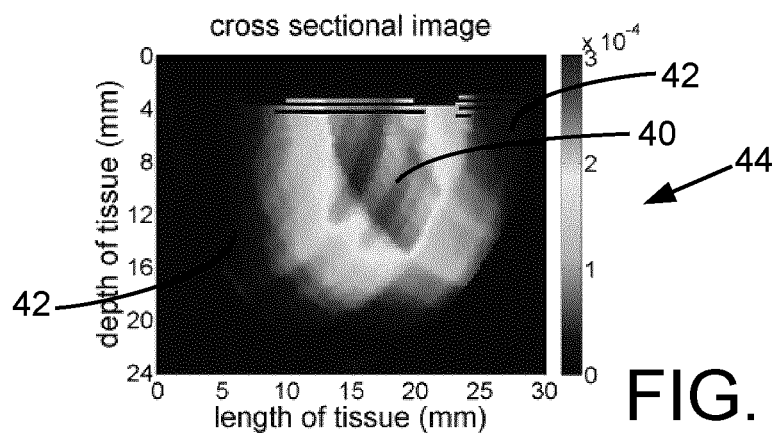
FIG. 9a is a cross-sectional image produced by the prototypical system shown in FIG. 3 when the probe is emitting electromagnetic radiation at 690 nm and is located along the center of the breast phantom's hole containing a protein assay reagent.
Figure 9B:
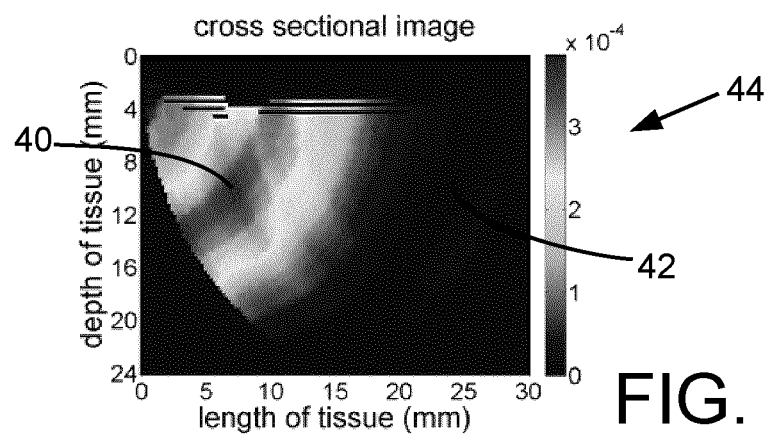
FIG. 9b is a cross-sectional image produced by the prototypical system shown in FIG. 3 when the probe is emitting electromagnetic radiation at 690 nm and is located to the left of the breast phantom's hole containing the protein assay reagent.
Figure 9C:
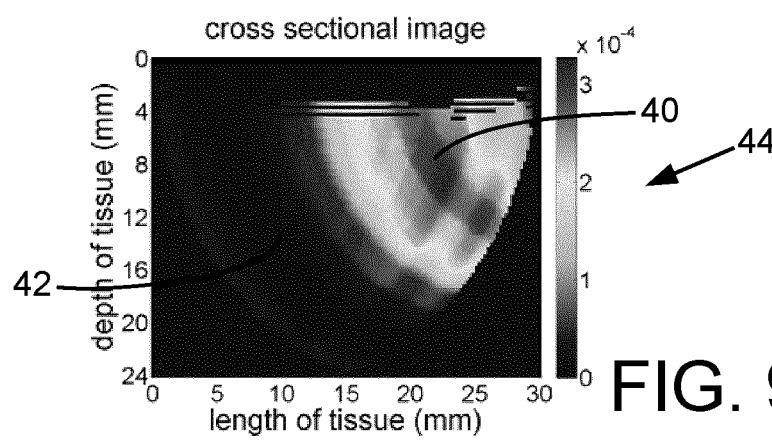
FIG. 9c is a cross-sectional image produced by the prototypical system shown in FIG. 3 when the probe is emitting electromagnetic radiation at 690 nm and is located to the right of the breast phantom's hole containing the protein assay reagent.

In the second experiment, we evaluated performance of the probe 10 to accurately create a separate image for different absorbers such as Hb and $HbO_2$. Therefore, we used protein assay reagent (PAR) to form inhomogeneity inside the phantom which has similar optical properties to $HbO_2$ in the NIR spectrum range. We used a solution of 1.5 mL Pierce™ 660 nm PAR (Thermo Scientific™ Inc.) mixed with 10 μL Pre-diluted protein assay standards: Bovine Serum Albumin (BSA), with 1000 μg/mL in 0.9% saline and 0.05% sodium azide to make a PAR. The absorption coefficient of RBSA at 690 nm wavelength is 0.17 mm$^{-1}$ which is much higher than its absorption coefficient at 750 nm, 800 nm and 850 nm (0.015 mm$^{-1}$). FIGS. 9a, 9b, and 9c show cross-sectional images 44 while the probe 10 is placed on different locations of the phantom while the 690 nm light source is illuminated.

Figure 10A:
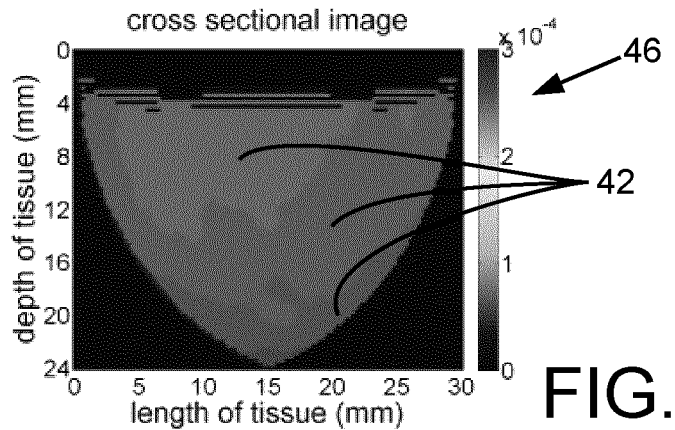
FIG. 10a is a cross-sectional image produced by the prototypical system shown in FIG. 3 when the probe is emitting electromagnetic radiation at 800 nm and is located along the center of the breast phantom's hole containing the protein assay reagent.
Figure 10B:
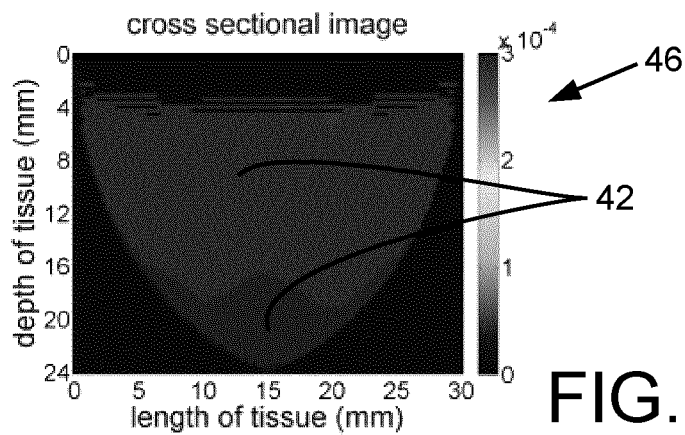
FIG. 10b is a cross-sectional image produced by the prototypical system shown in FIG. 3 when the probe is emitting electromagnetic radiation at 800 nm and is located to the left of the breast phantom's hole containing the protein assay reagent.
Figure 10C:
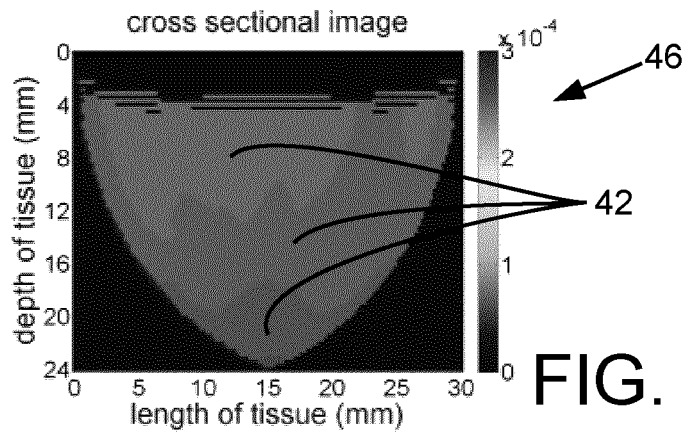
FIG. 10c is a cross-sectional image produced by the prototypical system shown in FIG. 3 when the probe is emitting electromagnetic radiation at 800 nm and is located to the right of the breast phantom's hole containing the protein assay reagent.
Figure 11A:
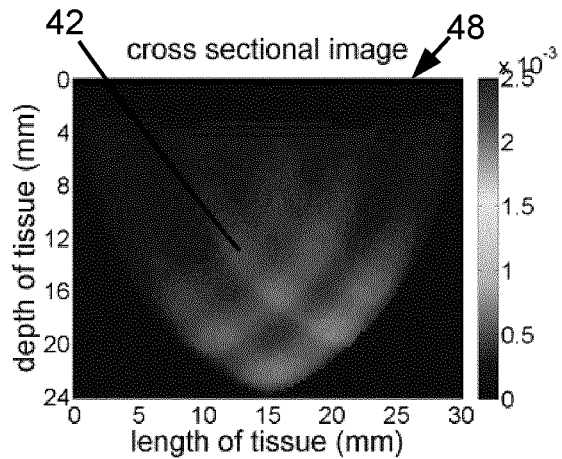
FIG. 11a is a cross-sectional image produced by the prototypical system shown in FIG. 3, showing reddish areas or lack thereof corresponding to the location of the breast phantom's hole containing a reference solution with India black ink in the concentration of 0.125 ml/l when the prototypical handheld probe is emitting electromagnetic radiation at 690 nm.
Figure 11B:
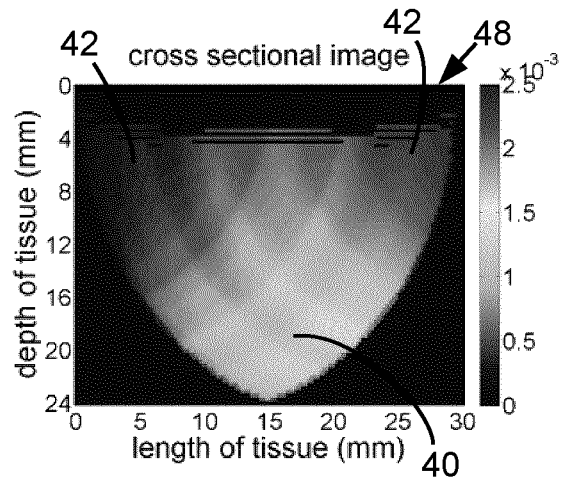
FIG. 11b is a cross-sectional image produced by the prototypical system shown in FIG. 3, showing reddish areas or lack thereof corresponding to the location of the breast phantom's hole containing the reference solution with India black ink in the concentration of 0.25 ml/l when the prototypical handheld probe is emitting electromagnetic radiation at 690 nm.
Figure 11C:
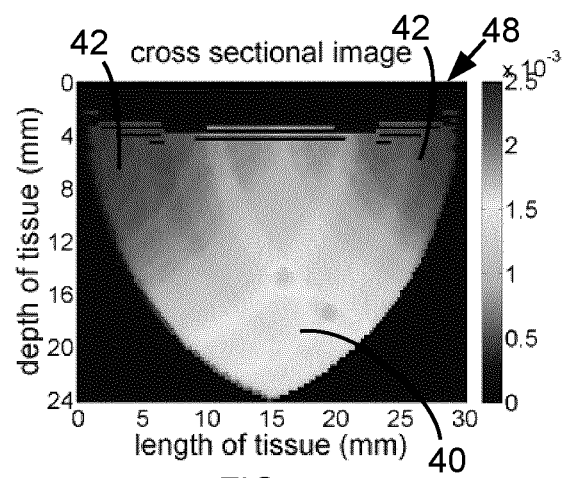
FIG. 11c is a cross-sectional image produced by the prototypical system shown in FIG. 3, showing reddish areas or lack thereof corresponding to the location of the breast phantom's hole containing the reference solution with India black ink in the concentration of 0.375 ml/l when the prototypical handheld probe is emitting electromagnetic radiation at 690 nm.
Figure 11D:
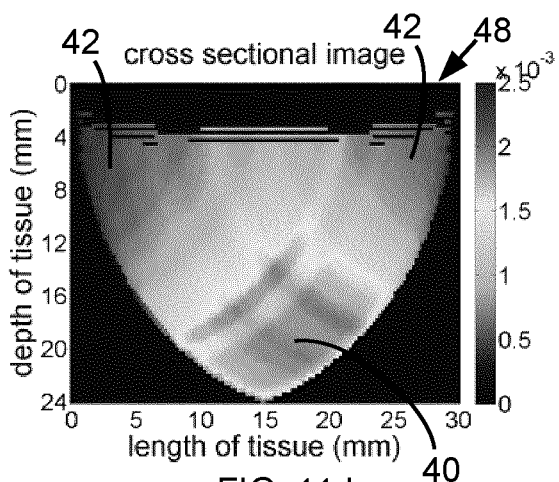
FIG. 11d is a cross-sectional image produced by the prototypical system shown in FIG. 3, showing reddish areas or lack thereof corresponding to the location of the breast phantom's hole containing the reference solution with India black ink in the concentration of 0.5 ml/l when the prototypical handheld probe is emitting electromagnetic radiation at 690 nm.
Figure 11E:
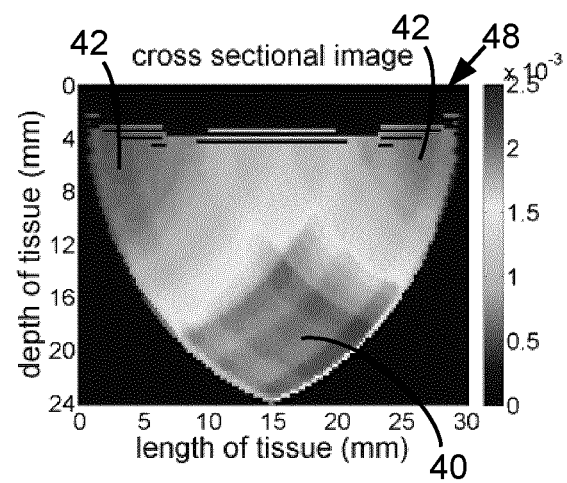
FIG. 11e is a cross-sectional image produced by the prototypical system shown in FIG. 3, showing reddish areas or lack thereof corresponding to the location of the breast phantom's hole containing the reference solution with India black ink in the concentration of 0.625 ml/l when the prototypical handheld probe is emitting electromagnetic radiation at 690 nm.
Figure 11F:
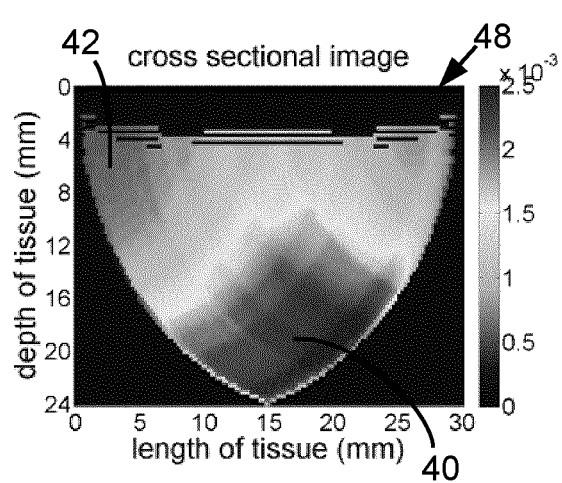
FIG. 11f is a cross-sectional image produced by the prototypical system shown in FIG. 3, showing reddish areas or lack thereof corresponding to the location of the breast phantom's hole containing the reference solution with India black ink in the concentration of 0.75 ml/l when the prototypical handheld probe is emitting electromagnetic radiation at 690 nm.
Figure 12A:
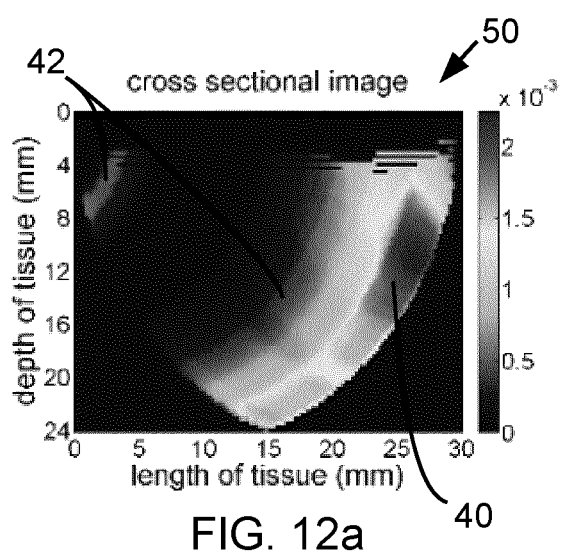
FIG. 12a is a sectional image associated with patient case 1, a wavelength of 690 nm, and the left breast of patient 1.
Figure 12B:
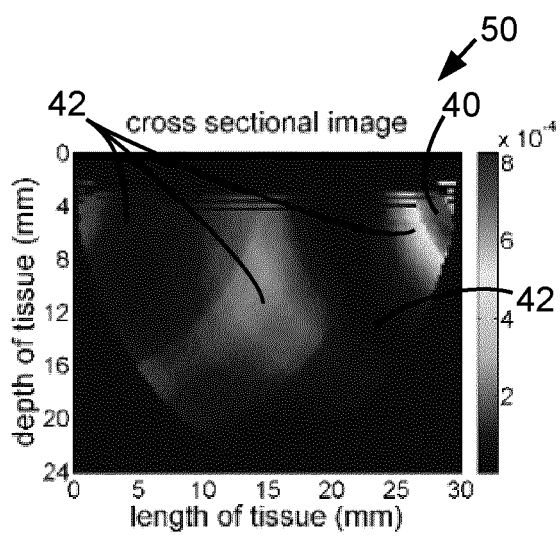
FIG. 12b is a sectional image associated with patient case 1, a wavelength of 690 nm, and the right breast of patient 1.
Figure 12C:
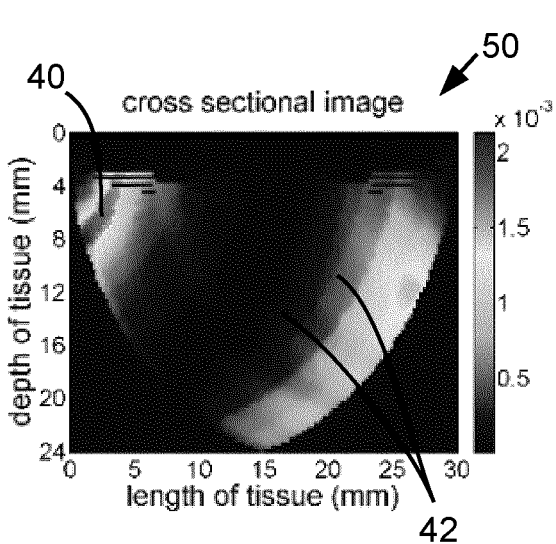
FIG. 12c is a sectional image associated with patient case 1, a wavelength of 750 nm, and the left breast of patient 1.
Figure 12D:
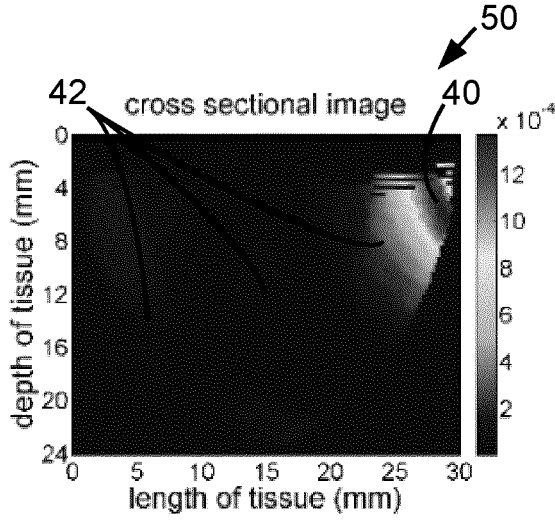
FIG. 12d is a sectional image associated with patient case 1, a wavelength of 750 nm, and the right breast of patient 1.
Figure 12E:
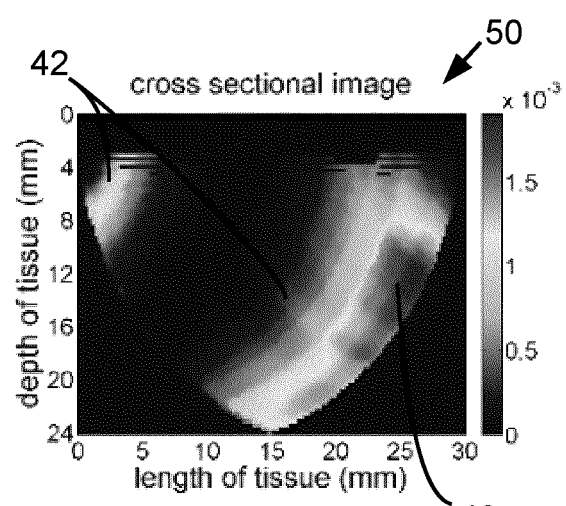
FIG. 12e is a sectional image associated with patient case 1, a wavelength of 800 nm, and the left breast of patient 1.
Figure 12F:
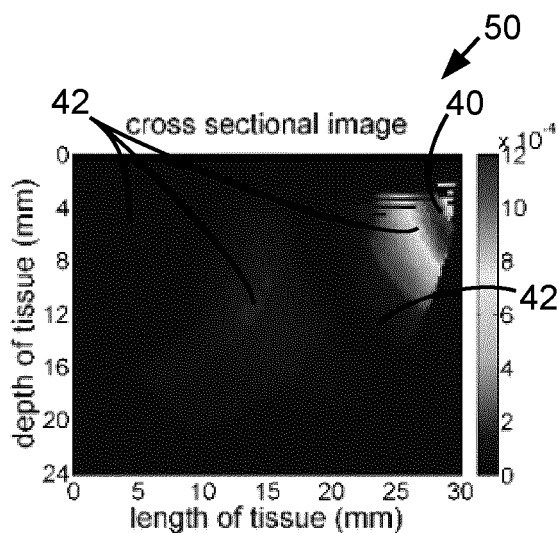
FIG. 12f is a sectional image associated with patient case 1, a wavelength of 800 nm, and the right breast of patient 1.
Figure 12G:
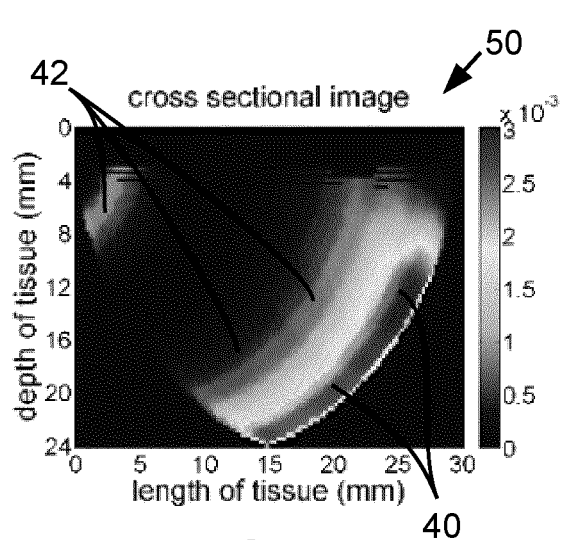
FIG. 12g is a sectional image associated with patient case 1, a wavelength of 850 nm, and the left breast of patient 1.
Figure 12H:
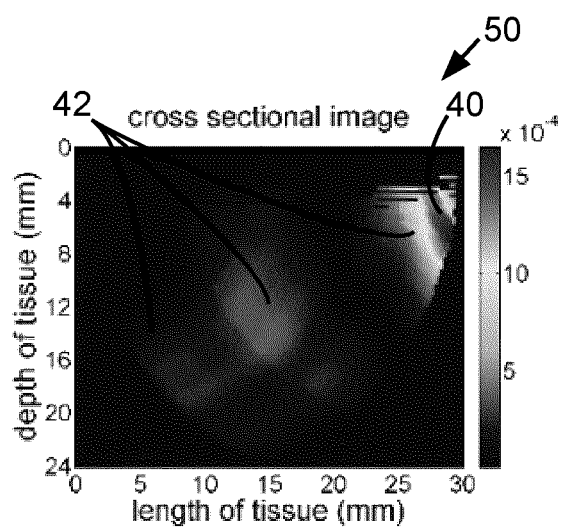
FIG. 12h is a sectional image associated with patient case 1, a wavelength of 850 nm, and the right breast of patient 1.
Figure 13A:
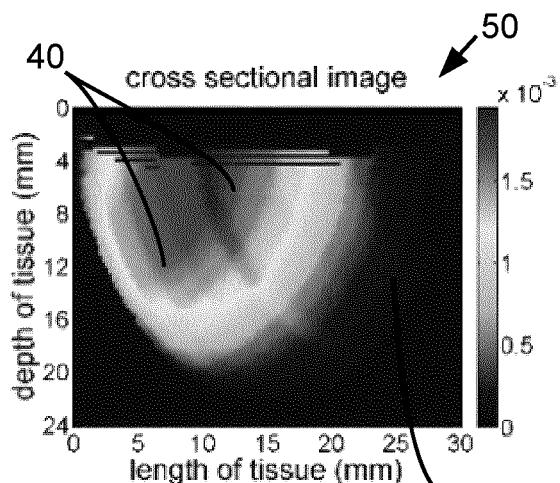
FIG. 13a is a sectional image associated with patient case 2, a wavelength of 690 nm, and the left breast of patient 2.
Figure 13B:
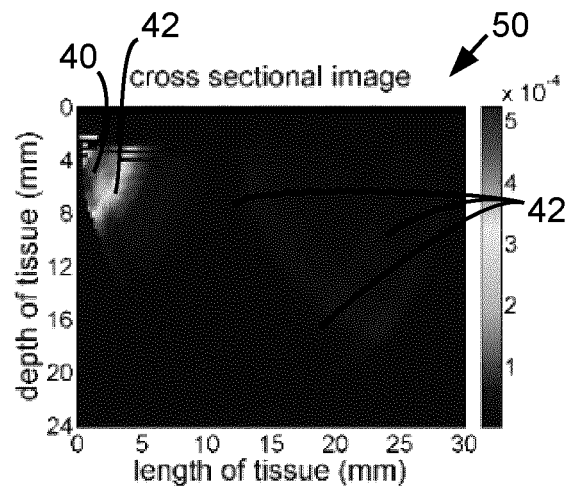
FIG. 13b is a sectional image associated with patient case 2, a wavelength of 690 nm, and the right breast of patient 2.
Figure 13C:
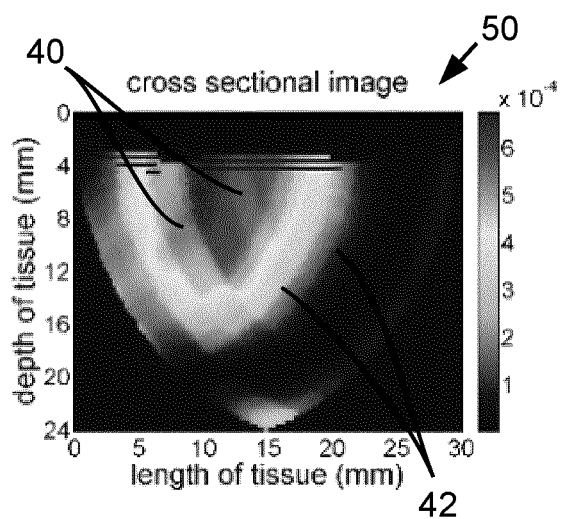
FIG. 13c is a sectional image associated with patient case 2, a wavelength of 750 nm, and the left breast of patient 2.
Figure 13D:
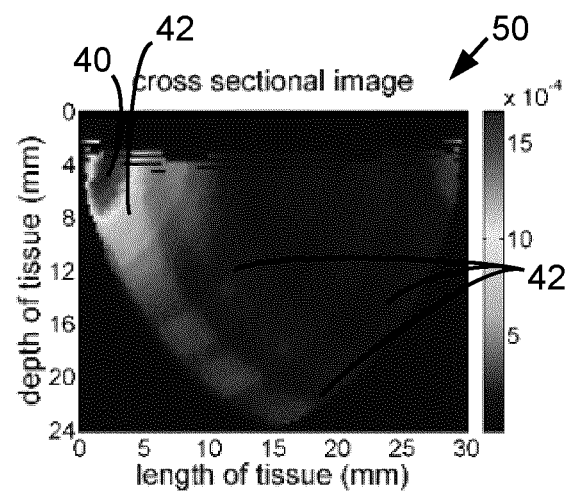
FIG. 13d is a sectional image associated with patient case 2, a wavelength of 750 nm, and the right breast of patient 2.
Figure 13E:
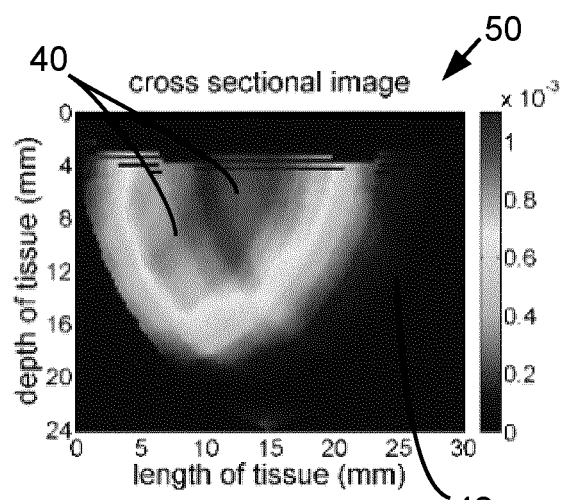
FIG. 13e is a sectional image associated with patient case 2, a wavelength of 800 nm, and the left breast of patient 2.
Figure 13F:
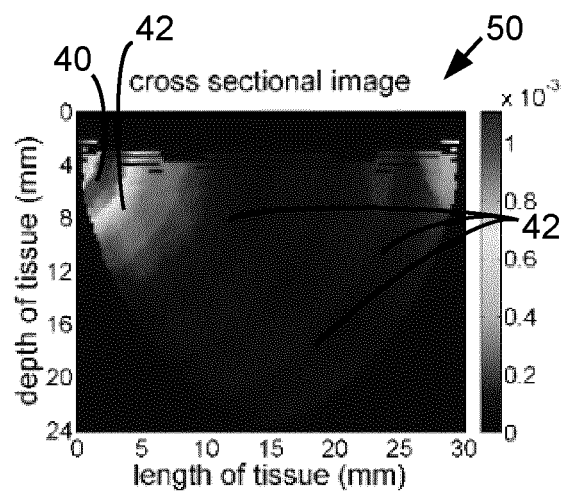
FIG. 13f is a sectional image associated with patient case 2, a wavelength of 800 nm, and the right breast of patient 2.
Figure 13G:
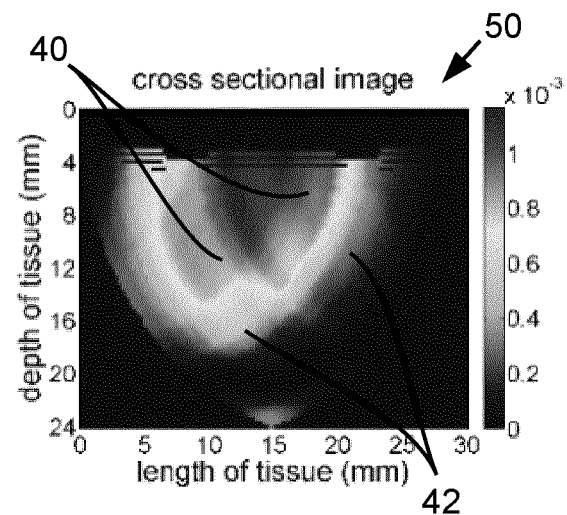
FIG. 13g is a sectional image associated with patient case 2, a wavelength of 850 nm, and the left breast of patient 2.
Figure 13H:
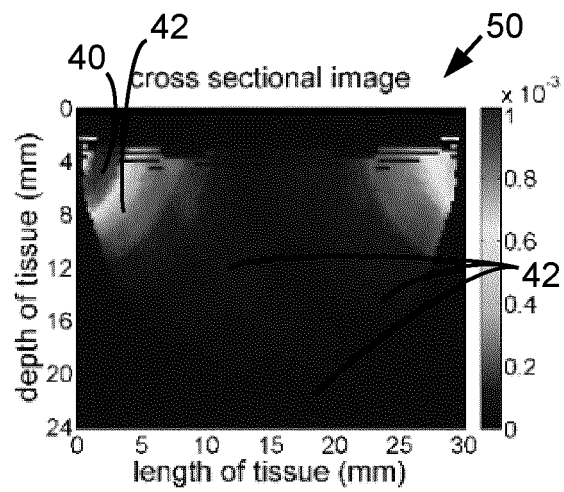
FIG. 13h is a sectional image associated with patient case 2, a wavelength of 850 nm, and the right breast of patient 2.
Figure 14A:
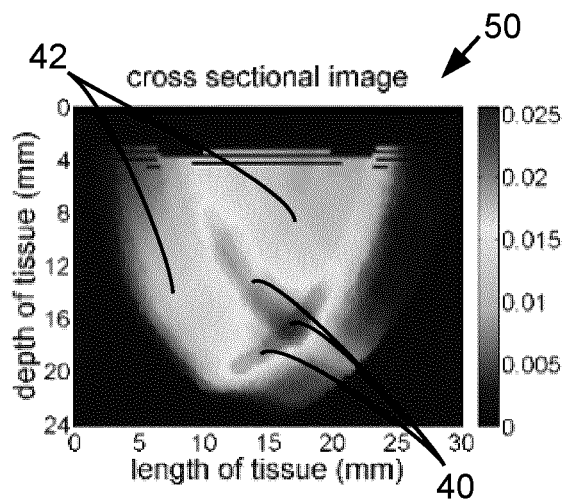
FIG. 14a is a sectional image associated with patient case 3, a wavelength of 690 nm, and the left breast of patient 3.
Figure 14B:
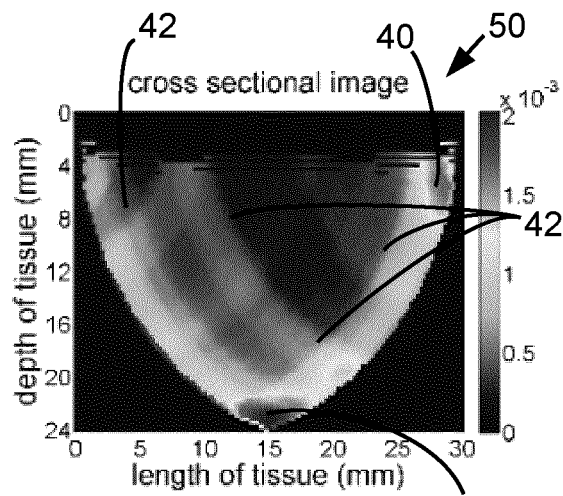
FIG. 14b is a sectional image associated with patient case 3, a wavelength of 690 nm, and the right breast of patient 3.
Figure 14C:
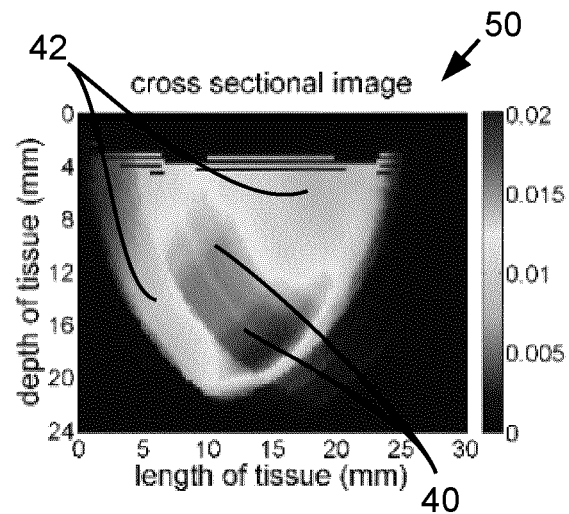
FIG. 14c is a sectional image associated with patient case 3, a wavelength of 750 nm, and the left breast of patient 3.
Figure 14D:
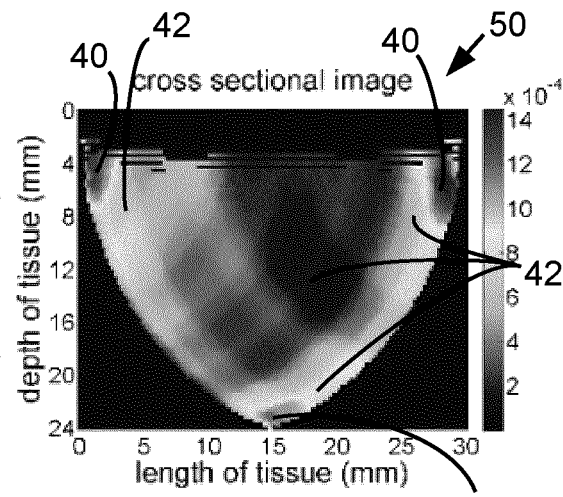
FIG. 14d is a sectional image associated with patient case 3, a wavelength of 750 nm, and the right breast of patient 3.
Figure 14E:
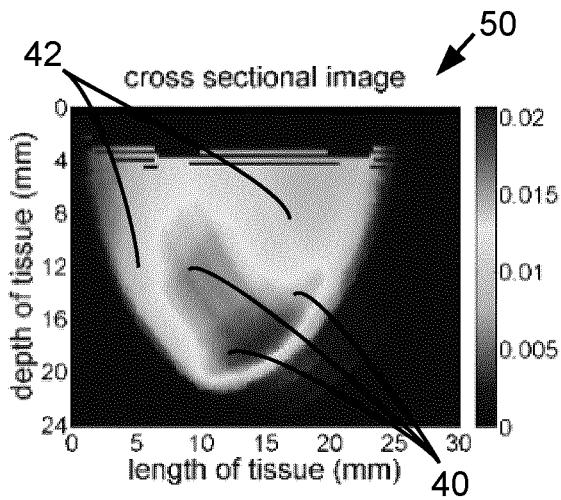
FIG. 14e is a sectional image associated with patient case 3, a wavelength of 800 nm, and the left breast of patient 3.
Figure 14F:
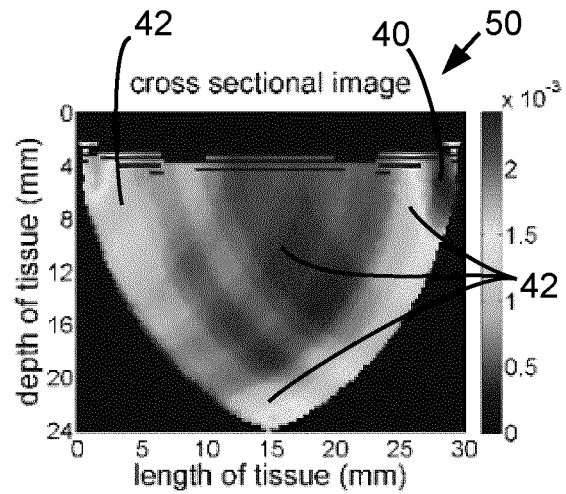
FIG. 14f is a sectional image associated with patient case 3, a wavelength of 800 nm, and the right breast of patient 3.
Figure 14G:
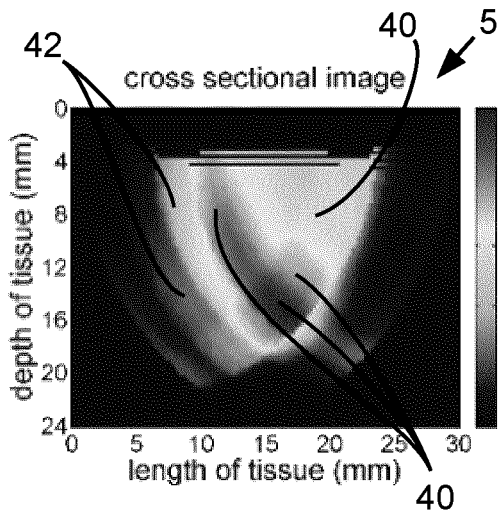
FIG. 14g is a sectional image associated with patient case 3, a wavelength of 850 nm, and the left breast of patient 3.
Figure 14H:
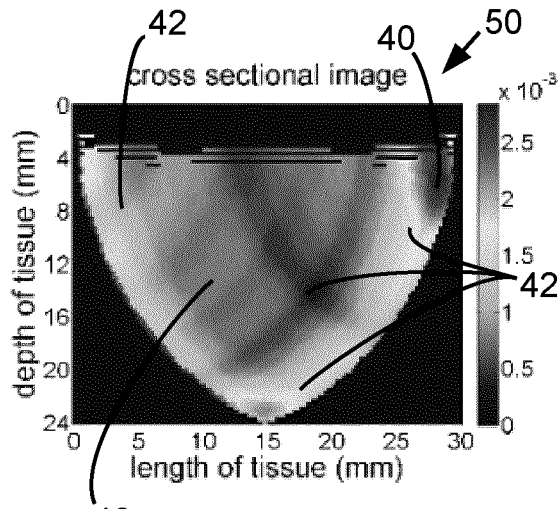
FIG. 14h is a sectional image associated with patient case 3, a wavelength of 850 nm, and the right breast of patient 3.
Figure 15A:
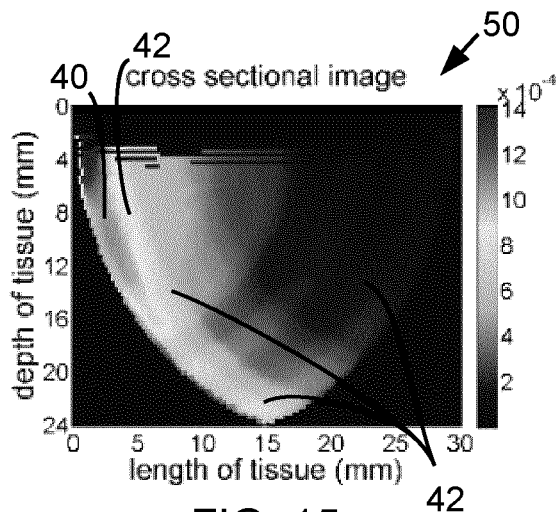
FIG. 15a is a sectional image associated with patient case 4, a wavelength of 690 nm, and the left breast of patient 4.
Figure 15B:
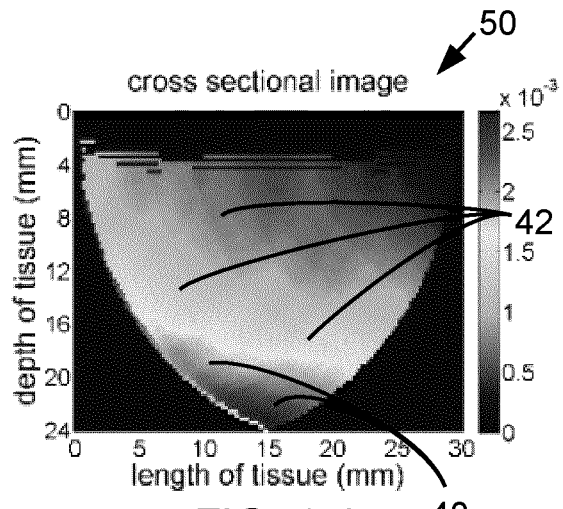
FIG. 15b is a sectional image associated with patient case 4, a wavelength of 690 nm, and the right breast of patient 4.
Figure 15C:
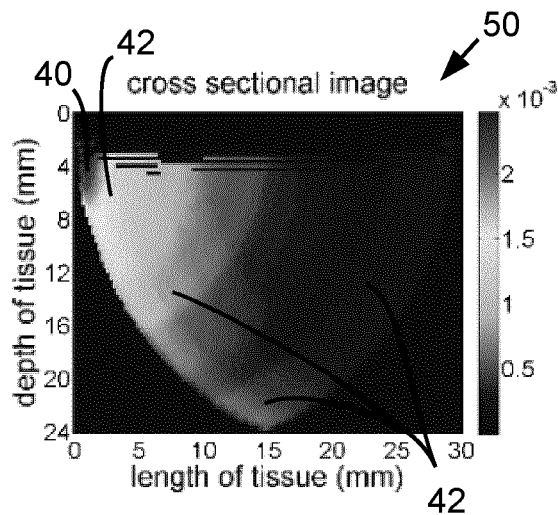
FIG. 15c is a sectional image associated with patient case 4, a wavelength of 750 nm, and the left breast of patient 4.
Figure 15D:
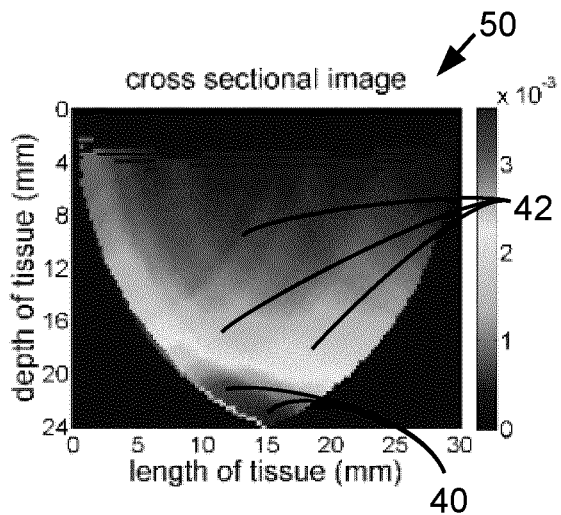
FIG. 15d is a sectional image associated with patient case 4, a wavelength of 750 nm, and the right breast of patient 4.
Figure 15E:
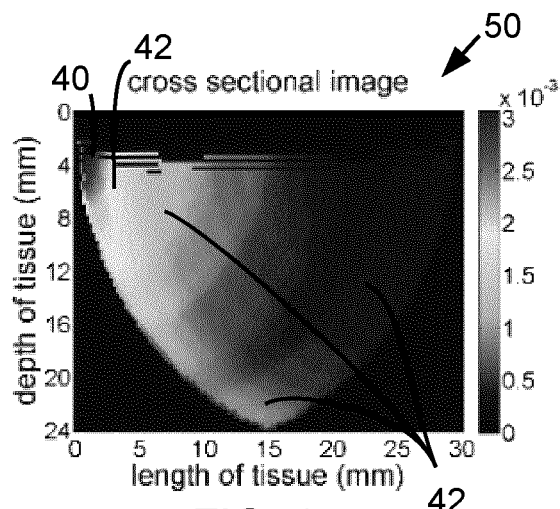
FIG. 15e is a sectional image associated with patient case 4, a wavelength of 800 nm, and the left breast of patient 4.
Figure 15F:
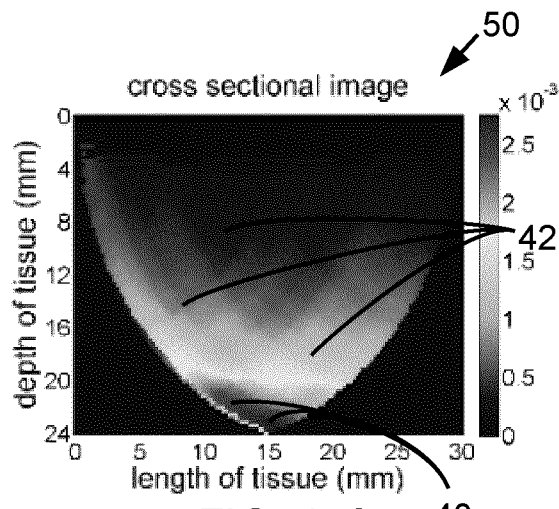
FIG. 15f is a sectional image associated with patient case 4, a wavelength of 800 nm, and the right breast of patient 4.
Figure 15G:
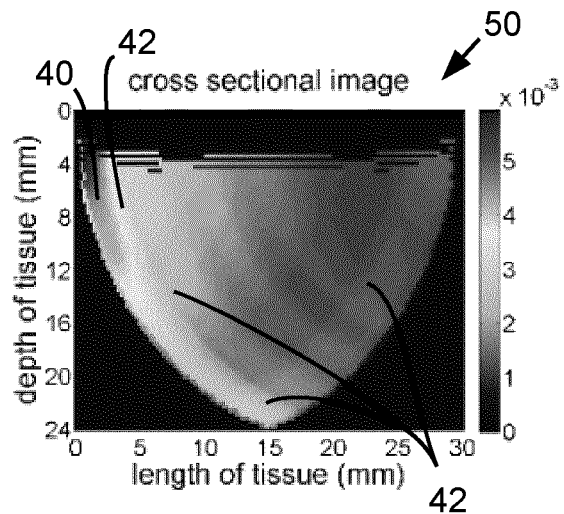
FIG. 15g is a sectional image associated with patient case 4, a wavelength of 850 nm, and the left breast of patient 4.
Figure 15H:
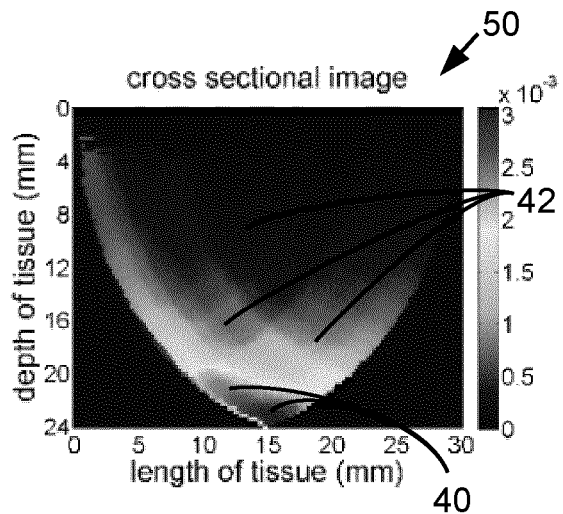
FIG. 15h is a sectional image associated with patient case 4, a wavelength of 850 nm, and the right breast of patient 4.
Figure 16A:
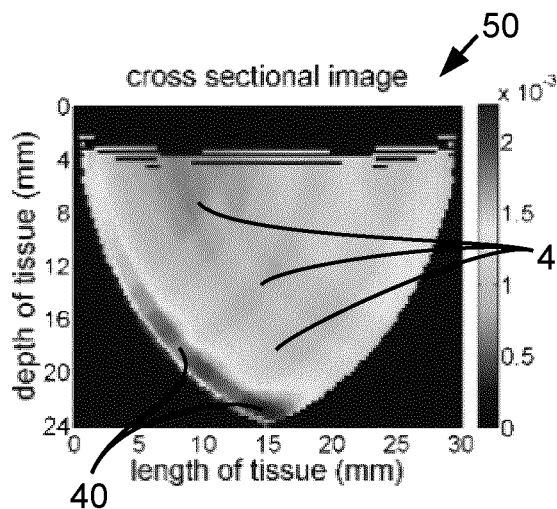
FIG. 16a is a sectional image associated with patient case 5, a wavelength of 690 nm, and the left breast of patient 5.
Figure 16B:
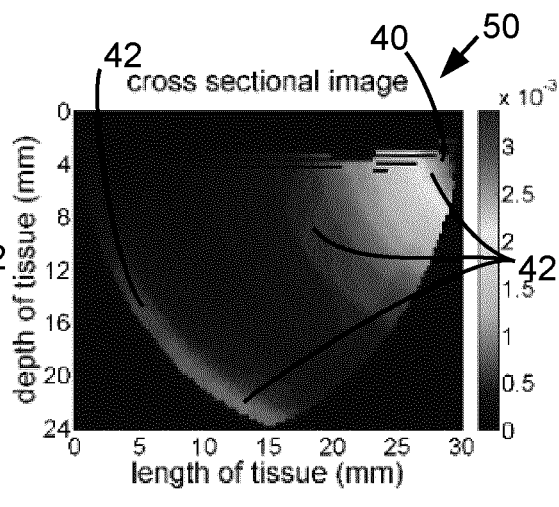
FIG. 16b is a sectional image associated with patient case 5, a wavelength of 690 nm, and the right breast of patient 5.
Figure 16C:
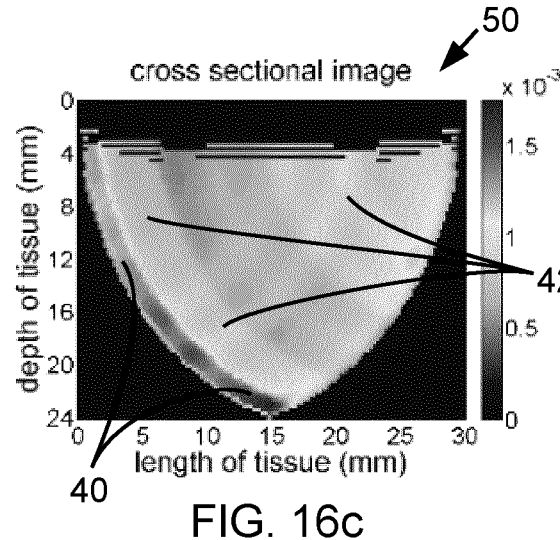
FIG. 16c is a sectional image associated with patient case 5, a wavelength of 750 nm, and the left breast of patient 5.
Figure 16D:
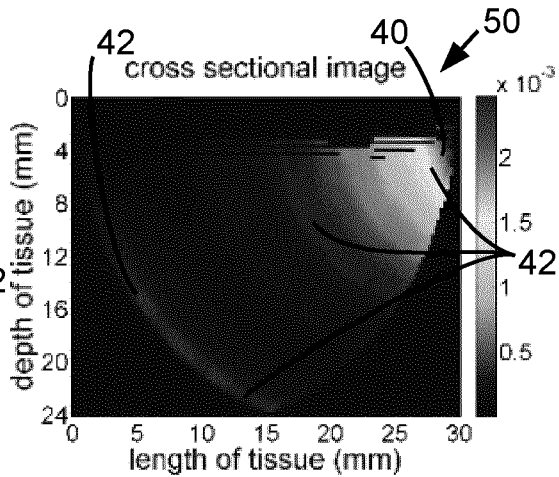
FIG. 16d is a sectional image associated with patient case 5, a wavelength of 750 nm, and the right breast of patient 5.
Figures 16E, 16F:
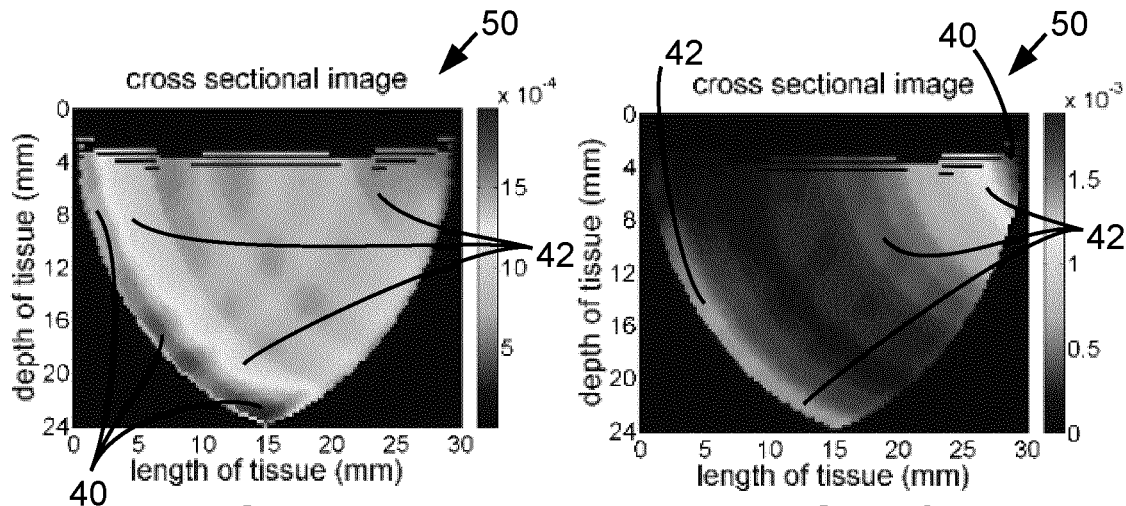
FIG. 16e is a sectional image associated with patient case 5, a wavelength of 800 nm, and the left breast of patient 5.
FIG. 16f is a sectional image associated with patient case 5, a wavelength of 800 nm, and the right breast of patient 5.
Figures 16G, 16H:
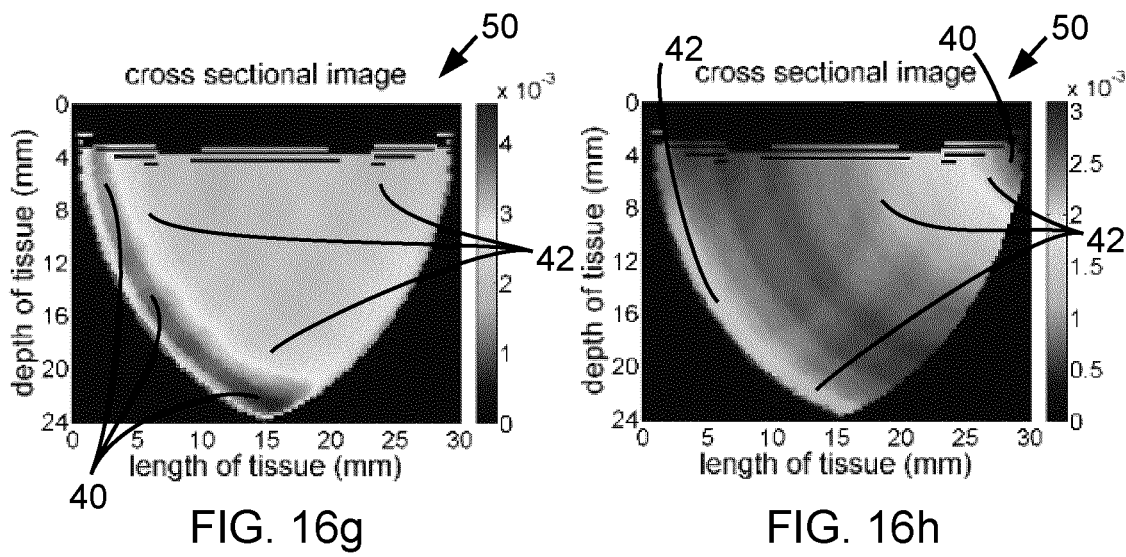
FIG. 16g is a sectional image associated with patient case 5, a wavelength of 850 nm, and the left breast of patient 5.
FIG. 16h is a sectional image associated with patient case 5, a wavelength of 850 nm, and the right breast of patient 5.

Since, absorption coefficient of the RBSA is much higher than surrounded material the probe 10 can capture this difference. FIGS. 9a, 9b, and 9c show reddish area(s) 40 corresponding to the locations (centrally aligned, to the left, and to the right) of the breast phantom's hole 36 containing the PAR, respectively, in contrast to non-reddish area(s) 42 that can be seen in FIGS. 9a, 9b, and 9c. But for the 750 nm, 800 nm and 850 nm, the probe 10 did not capture the inhomogeneity due to similar absorption coefficient of RBSA with surrounded material as demonstrated by the images 46 shown in FIGS. 10a, 10b, and 10c for the wavelength of 800 nm in which a reddish area 40 is not visible. The three cross-sectional images of FIGS. 10a, 10b, and 10c produced by use of the DOB-Scan probe 10 show an absence of reddish areas 40 corresponding to the location of the breast phantom's hole containing the PAR when the prototypical handheld probe 10 is emitting electromagnetic radiation at 800 nm and is located: a) along the center of the hole 36, b) to the left of the hole 36 center, and c) to the right of the hole 36 center. In contrast to the absence of reddish areas 40, only non-reddish areas 42 are predominantly visible in FIGS. 10a, 10b, 10c.

In order to evaluate the probe's effectiveness in monitoring the effect of therapy on the size of a tumor, we have done one more experiment in which the absorption coefficient of a cancerous-mimicking phantom 14 is gradually increased by adding India black ink to a reference solution of water and Intralipid® (50 ml/l). In this experiment, India black ink was added in 0.125 ml/l increments from 0.125 ml/l to 0.75 ml/l, however, the scattering coefficient of the medium was not affected by increasing the ink concentration.

Four images are reconstructed for each step. Therefore 24 images are created, in total. As mentioned before, we just present one image 48 (690 nm) for each step, because India black ink has a flat absorption spectrum in the NIR range, which is shown in FIGS. 11a to 11f. That is, FIGS. 11a to 11f are six cross-sectional images produced by the probe 10 showing reddish areas 40 corresponding to the location of the breast phantom's hole containing varying concentrations of India black ink when the handheld probe 10 is emitting electromagnetic radiation at 690 nm.

The reddish areas 40 and the non-reddish areas 42 in images 48 of FIGS. 11a to 11f clearly show that the DOB-Scan probe 10 is capable of capturing any changes in the absorption coefficient of the tumor phantom 14. Therefore, the DOB-Scan probe 10 can be used to monitor the effect of the therapy on tumor size.

The performance of an exemplary prototype of the probe 10 was evaluated by testing it on breast tissue-like phantom 14. The test results of the exemplary probe being used on breast tissue-like phantom show that the probe 10 can create functional images and chromophores composition images of the phantom 14.

Initial Clinical Study

Extended data collected for cancerous tissue further demonstrates the probe's performance in its prototypical form. A technique to identify malignant breast tumors using contralateral healthy body tissue as a control is used to produce preliminary results for ten cases presented below.

A clinical study was performed on ten patients who have been diagnosed with breast cancer. Before any measurements are taken, subjects' height, weight, age and gender were recorded. Details of subjects' breast cancer (for example, type of cancer, date of diagnosis, etc.) were also recorded. The subjects were asked to lie down on their back and then we placed the probe on the location of the breast that had cancer. The skin to which the probe is located is cleaned with alcohol prep pads. The same procedure has been done on the contralateral side of the breast. The test procedure takes approximately twenty minutes. We obtained preliminary data with DOB-Scan probe while that is located on the breast where diagnosed to have malignant tissue and its contralateral location on the healthy breast. Data gathered with cross sectional diffuse optical imaging modality processed and analysed to explore performance of the exemplary probes to detect and characterize malignant tissue in the breast, in-vivo.

The reconstructed preliminary images show that the DOB-San probe can distinguish the cancerous region from the surrounding healthy tissue. The cancerous region is observable in the images (red area) due to a higher level of absorption caused by higher levels of vascularization. The red area on the images reflexes location of anomaly tissue in the breast.

For each patient, two locations are scanned over cancerous lesion with the control as a contralateral healthy breast tissue. Four cross-sectional images are reconstructed for four NIR sources on each location. The test results below show that absorption coefficient of cancerous lesions are significantly higher than normal surrounding tissue. The main objective of this study was to validate the usability of developed DOB-Scan imaging set up to create cross-sectional images of the breast tissue and detect anomalies inside inhomogeneous breast tissue, based upon optical properties of the anomaly to the surrounding material.

Table 2 represents brief clinical reports for the patients who enrolled in the further clinical study.

TABLE 2

Brief clinical reports for ten patients enrolled in the study.

| Patient no. | age | Tumor position | Cancerous breast | Tumor size | Tumor type | Diagnosis tools |
|---|---|---|---|---|---|---|
| 1 | 53 | 10-12 o'clock | left | 2.5*0.8*0.8 | Invasive lobular carcinoma | Mammography |
| 2 | 62 | 3-4 o'clock | left | 2.2 × 1.7 × 17 cm | solid lobulated irregular mass | Mammography |
| 3 | 84 | 1 o'clock | left | 10 mm | ductal carcinoma | Mammography |
| 4 | 79 | 9 O'clock | right | 7 mm | Invasive mammary carcinoma | Mammography, MRI |
| 5 | 44 | 2 o'clock | left | 2.5 cm × 1.7 cm × 3.5 cm | lobulated irregular mass | Mammography |
| 6 | 42 | 1 o'clock | right | 24 mm in diameter | Solid mass with irregular margin | Mammography and US |
| 7 | 59 | 10-11 o'clock | right | 23*22*15 mm in diameter | lobulated irregular mass | Mammography |
| 8 | 56 | 12-1 o'clock | left | 1.6 cm in maximal dimension | Lobulated hypoechoic lesion | Mammography and US |
| 9 | 63 | 2 o'clock | left | 12 × 9 × 9 mm | Solid Lesions | Mammography and CBE |
| 10 | 53 | 5 o'clock | left | 1.7 × 1.2 × 2.4 cm | Invasive ductal carcinoma | Mammography and US |

FIGS. 12a to 12h, 13a to 13h, 14a to 14h, 15a to 15h, 16a to 16h, 17a to 17h, 18a to 18h, 19a to 19h, and 20a to 20h represent reconstructed images 50 for four different wavelengths while the probe 10 positioned on the location where diagnosed having a cancerous lesion and its contralateral position for 9 of the 10 patients tabulated above. The reddish area 40 on the images reflect the location of anomalous tissue, in contrast to the non-reddish areas 42.

Referring to FIGS. 12a to 20h, each breast has four images for four different wavelengths. Table 3 indicates the parameters associated with the Figures identified as "a" to "h" for each the Figure sets enumerated by the numbers 12 to 20. For example, FIG. 12a, FIG. 13a, and so on to FIG. 20a are each associated with the wavelength 690 nm and the left breast, while FIG. 12b, FIG. 13b, and so on to FIG. 20b are each associated with 690 nm and the right breast.

TABLE 3

Test parameters associated with FIGS. 12a to 20h

| Figure Identification | Wavelength | Breast |
|---|---|---|
| a | 690 nm | left |
| b | 690 nm | right |
| c | 750 nm | left |
| d | 750 nm | right |
| e | 800 nm | left |

TABLE 3-continued

Test parameters associated with FIGS. 12a to 20h

| Figure Identification | Wavelength | Breast |
|---|---|---|
| f | 800 nm | right |
| g | 850 nm | left |
| h | 850 nm | right |

Each of the ten cases are described below.

Case 1: There was two cancerous lesions in the left breast and the probe 10 located on the one located at 10 o'clock of the left breast. FIGS. 12a to 12h present that the probe 10 captured the tumor correctly. There are some reddish areas 40 on the healthy breast (FIGS. 12b, 12d, 12f, and 12h) which caused by saturation of the detector.

Case 2: There was two cancerous lesions in the left breast and the probe 10 located on the one located at 4 o'clock of the left breast. FIGS. 13a to 13h present that the probe 10 captured the tumor correctly and it is in line with mammography images. There are some reddish areas 40 on the healthy breast (FIGS. 13b, 13d, 13f, and 13h) which caused by saturation of the detector.

Case 3: There was a cancerous lesions in the left breast at 1 o'clock. FIGS. 14a to 14h presents that the probe 10 captured the tumor correctly and it is in line with mammography images. There are some reddish areas 40 on the healthy breast (FIGS. 14b, 14d, 14f, and 14h) which caused by saturation of the detector.

Case 4: There was a cancerous lesions in the right breast at 9 o'clock. This patient had large breasts with a cancerous lesion positioned near to the chest wall. In these cases, the probe 10 captures the cancerous lesion with difficulty due to the depth of the tumor in the breast (FIGS. 15b, 15d, 15f, and 15h). There are some reddish areas 40 on the healthy breast (FIGS. 15a, 15c, 15e, and 15g) which caused by saturation of the detector.

Case 5: There was a cancerous lesions in the left breast at 2 o'clock. Reconstructed images for the left breast of patient #5 (FIGS. 16a, 16c, 16e, and 16g) show that the absorption coefficient of the whole breast is unusually higher than for the malignant tissue. Medical advice from the patient's oncologists indicates there was a lobulated irregular large shadowing mass which had spread all over the left breast. For this reason, the probe 10 shows higher absorption coefficient whole over the breast. There are some reddish areas 40 on the healthy breast (FIGS. 16b, 16d, 16f, and 16h) which caused by saturation of the detector.

Figure 17A:
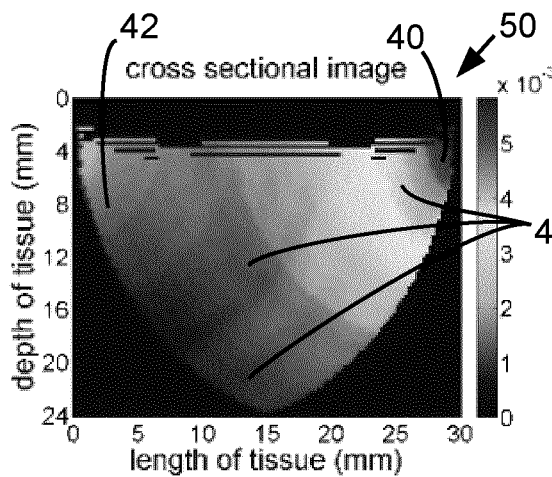
FIG. 17a is a sectional image associated with patient case 6, a wavelength of 690 nm, and the left breast of patient 6.
Figure 17B:
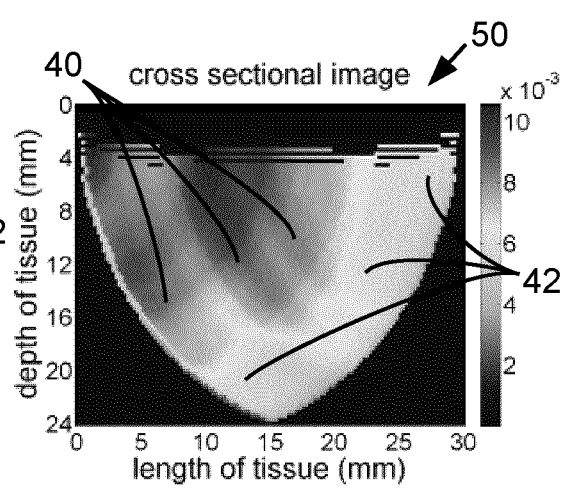
FIG. 17b is a sectional image associated with patient case 6, a wavelength of 690 nm, and the right breast of patient 6.
Figure 17C:
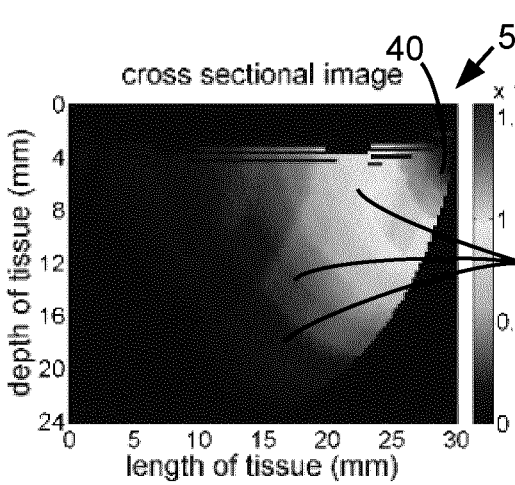
FIG. 17c is a sectional image associated with patient case 6, a wavelength of 750 nm, and the left breast of patient 6.
Figure 17D:
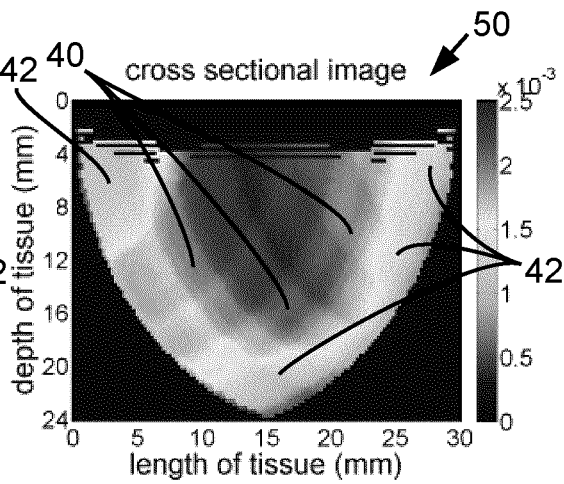
FIG. 17d is a sectional image associated with patient case 6, a wavelength of 750 nm, and the right breast of patient 6.
Figure 17E:
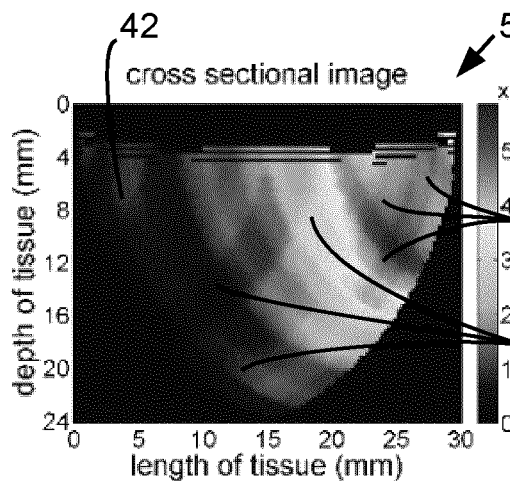
FIG. 17e is a sectional image associated with patient case 6, a wavelength of 800 nm, and the left breast of patient 6.
Figure 17F:
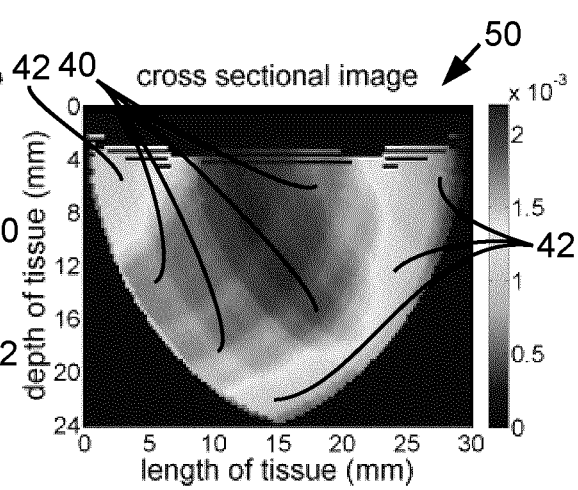
FIG. 17f is a sectional image associated with patient case 6, a wavelength of 800 nm, and the right breast of patient 6.
Figure 17G:
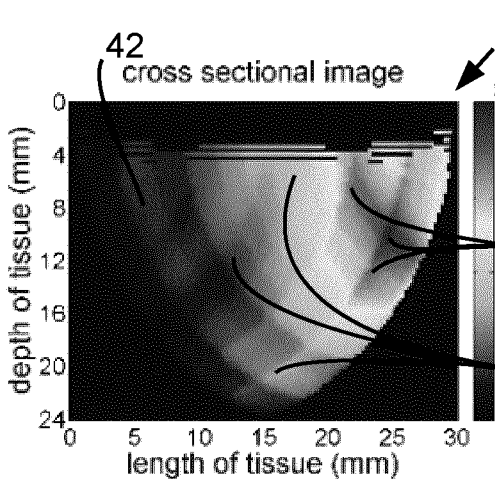
FIG. 17g is a sectional image associated with patient case 6, a wavelength of 850 nm, and the left breast of patient 6.
Figure 17H:
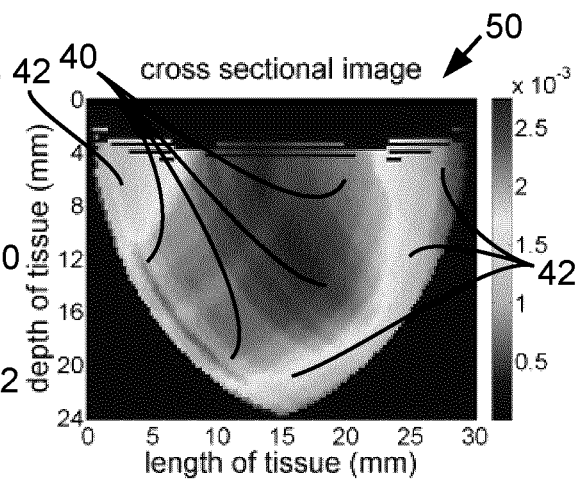
FIG. 17h is a sectional image associated with patient case 6, a wavelength of 850 nm, and the right breast of patient 6.
Figure 18A:
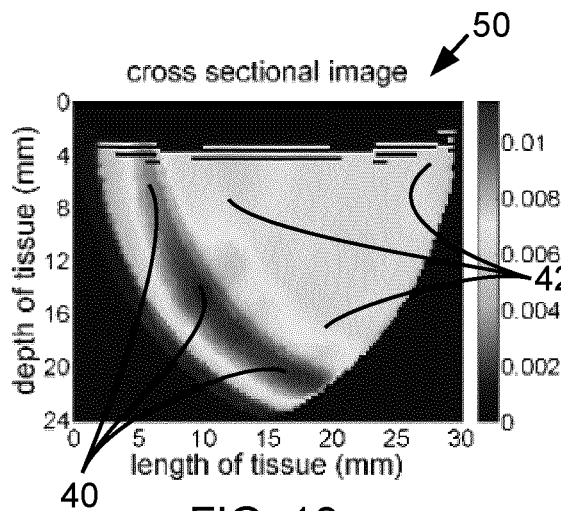
FIG. 18a is a sectional image associated with patient case 7, a wavelength of 690 nm, and the left breast of patient 7.
Figure 18B:
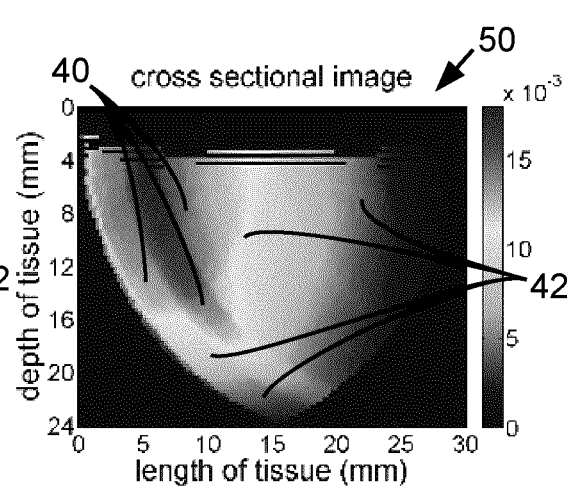
FIG. 18b is a sectional image associated with patient case 7, a wavelength of 690 nm, and the right breast of patient 7.
Figure 18C:
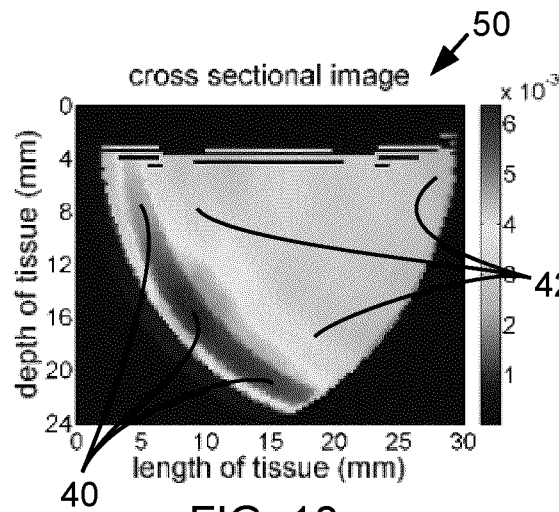
FIG. 18c is a sectional image associated with patient case 7, a wavelength of 750 nm, and the left breast of patient 7.
Figure 18D:
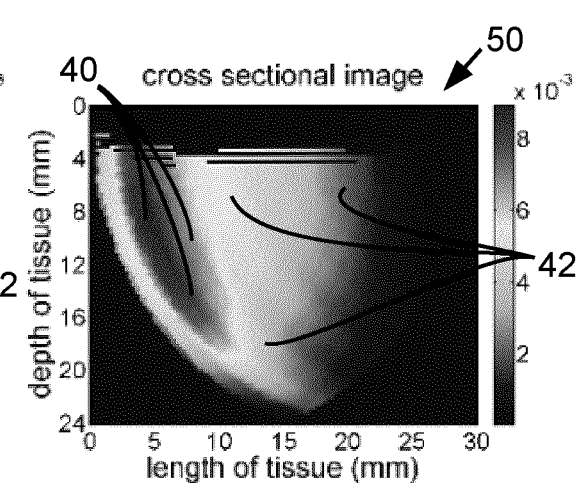
FIG. 18d is a sectional image associated with patient case 7, a wavelength of 750 nm, and the right breast of patient 7.
Figure 18E:
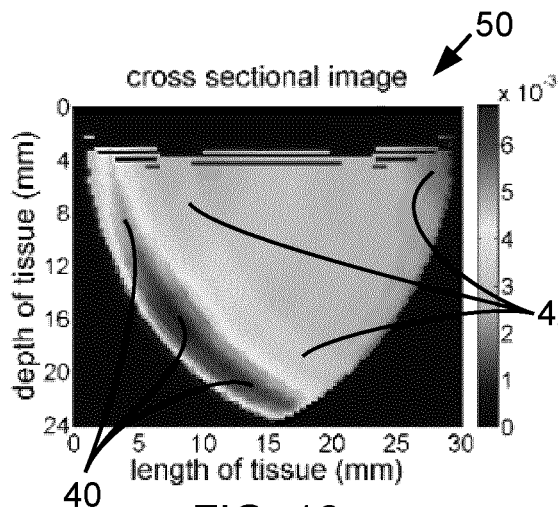
FIG. 18e is a sectional image associated with patient case 7, a wavelength of 800 nm, and the left breast of patient 7.
Figure 18F:
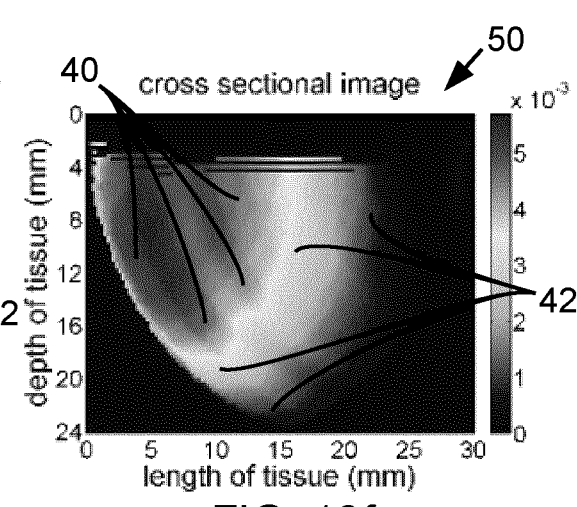
FIG. 18f is a sectional image associated with patient case 7, a wavelength of 800 nm, and the right breast of patient 7.
Figure 18G:
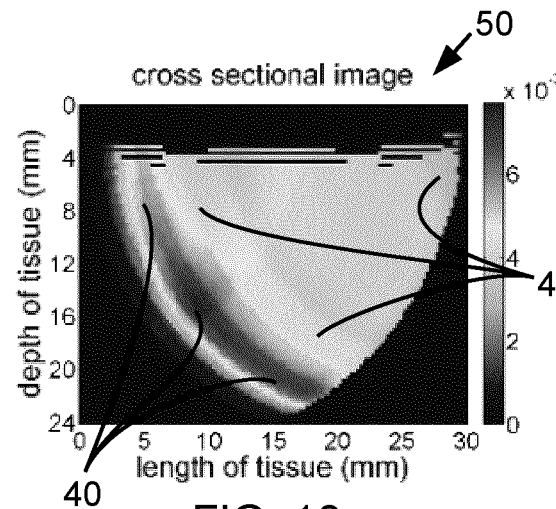
FIG. 18g is a sectional image associated with patient case 7, a wavelength of 850 nm, and the left breast of patient 7.
Figure 18H:
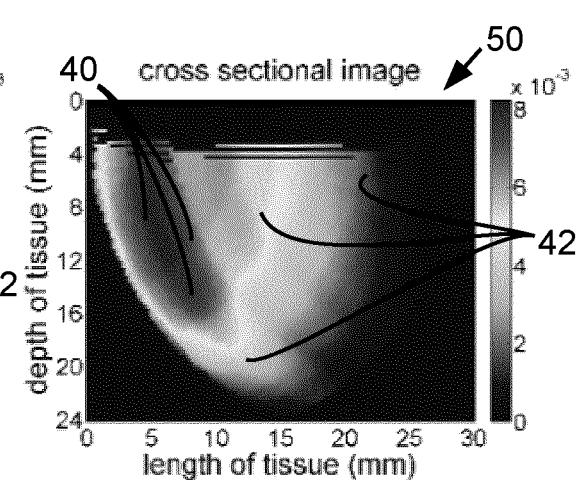
FIG. 18h is a sectional image associated with patient case 7, a wavelength of 850 nm, and the right breast of patient 7.
Figure 19A:
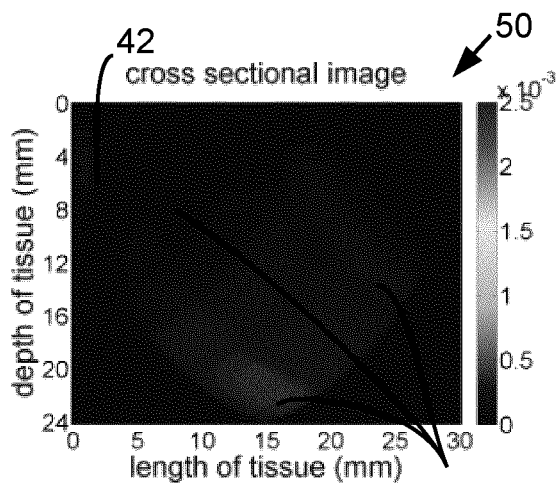
FIG. 19a is a sectional image associated with patient case 9, a wavelength of 690 nm, and the left breast of patient 9.
Figure 19B:
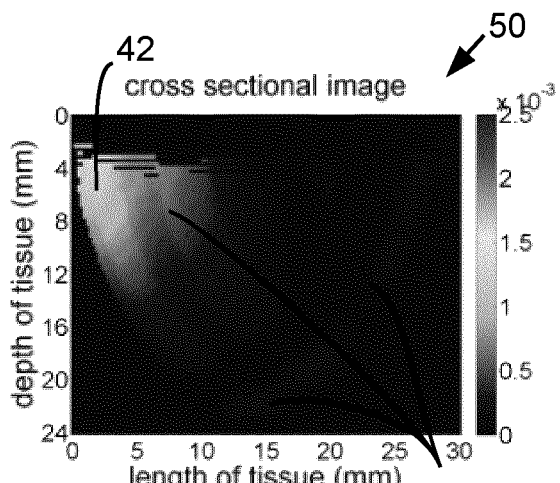
FIG. 19b is a sectional image associated with patient case 9, a wavelength of 690 nm, and the right breast of patient 9.
Figure 19C:
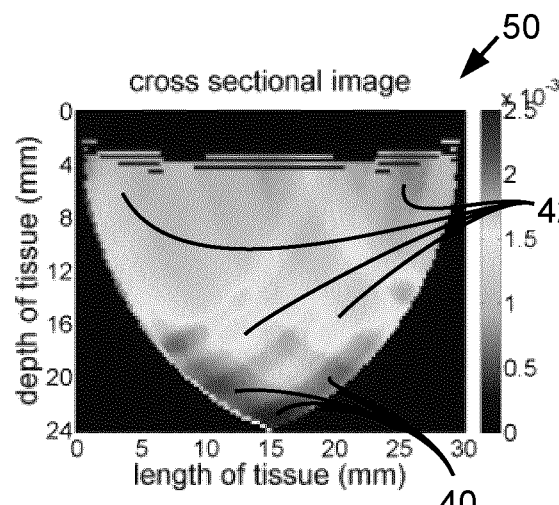
FIG. 19c is a sectional image associated with patient case 9, a wavelength of 750 nm, and the left breast of patient 9.
Figure 19D:
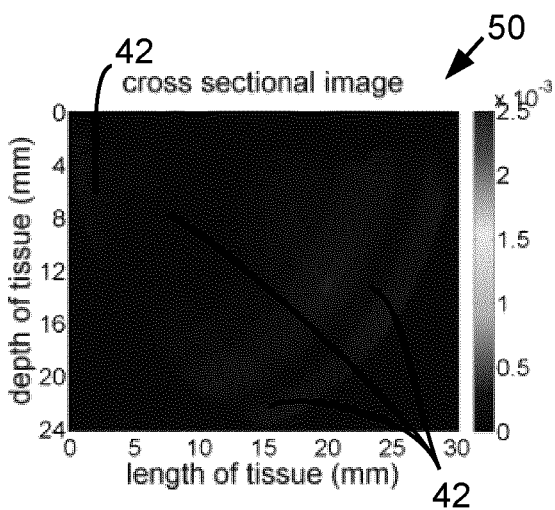
FIG. 19d is a sectional image associated with patient case 9, a wavelength of 750 nm, and the right breast of patient 9.
Figure 19E:
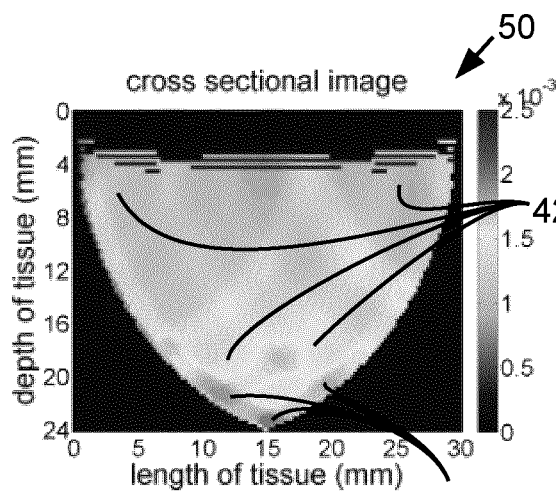
FIG. 19e is a sectional image associated with patient case 9, a wavelength of 800 nm, and the left breast of patient 9.
Figure 19F:
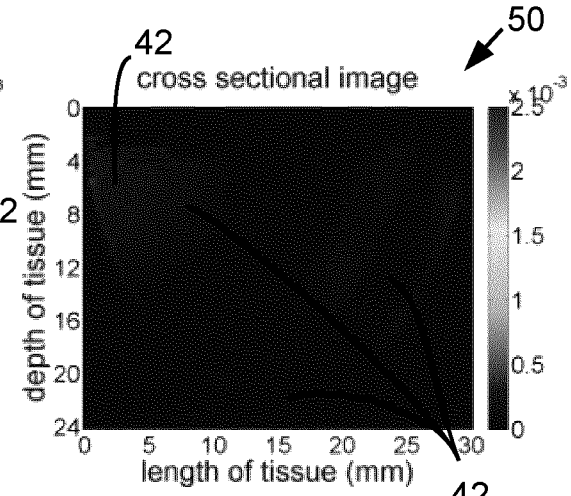
FIG. 19f is a sectional image associated with patient case 9, a wavelength of 800 nm, and the right breast of patient 9.
Figure 19G:
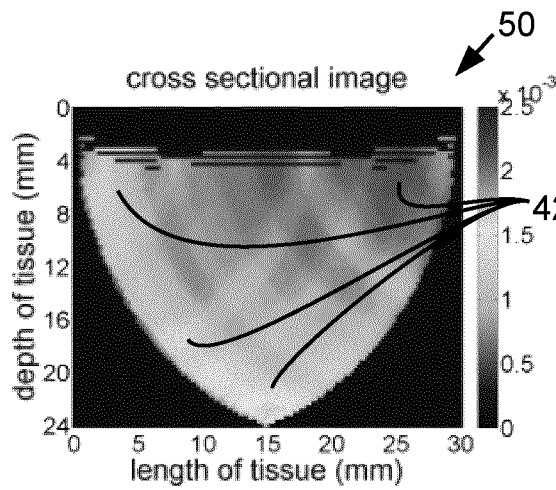
FIG. 19g is a sectional image associated with patient case 9, a wavelength of 850 nm, and the left breast of patient 9.
Figure 19H:
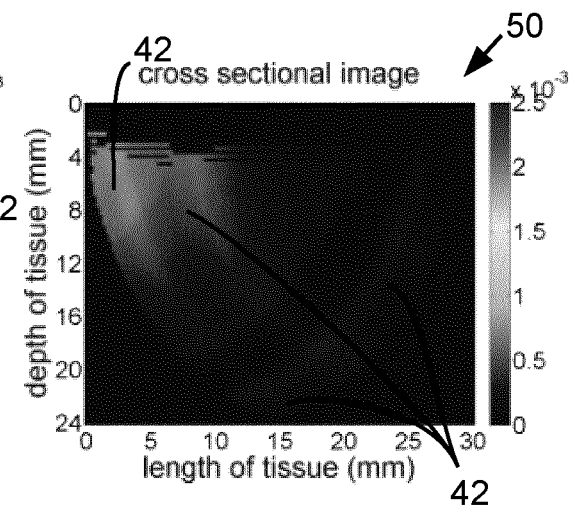
FIG. 19h is a sectional image associated with patient case 9, a wavelength of 850 nm, and the right breast of patient 9.
Figure 20A:
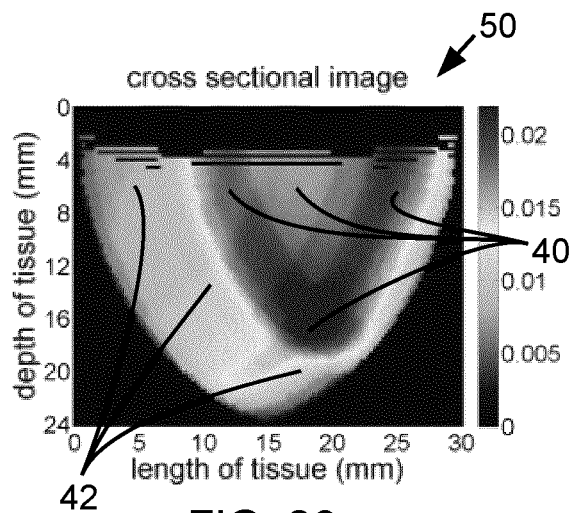
FIG. 20a is a sectional image associated with patient case 10, a wavelength of 690 nm, and the left breast of patient 10.
Figure 20B:
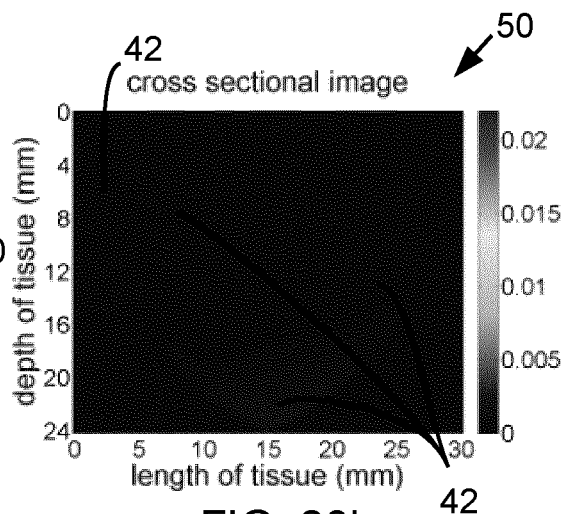
FIG. 20b is a sectional image associated with patient case 10, a wavelength of 690 nm, and the right breast of patient 10.
Figure 20C:
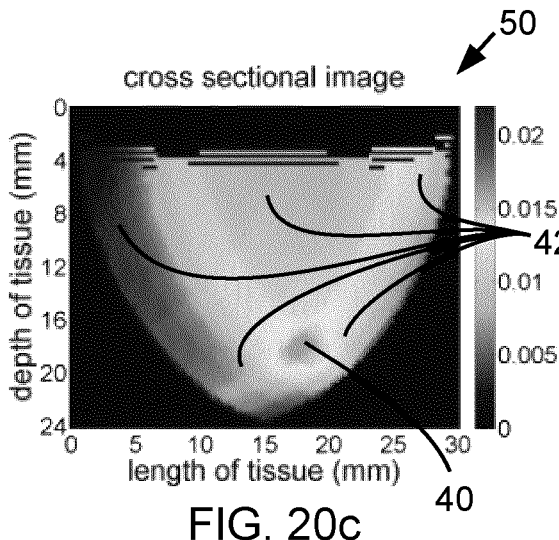
FIG. 20c is a sectional image associated with patient case 10, a wavelength of 750 nm, and the left breast of patient 10.
Figure 20D:
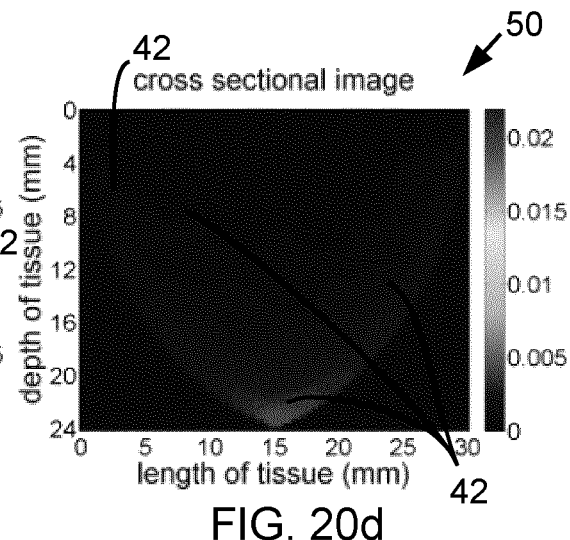
FIG. 20d is a sectional image associated with patient case 10, a wavelength of 750 nm, and the right breast of patient 10.
Figures 20E, 20F:
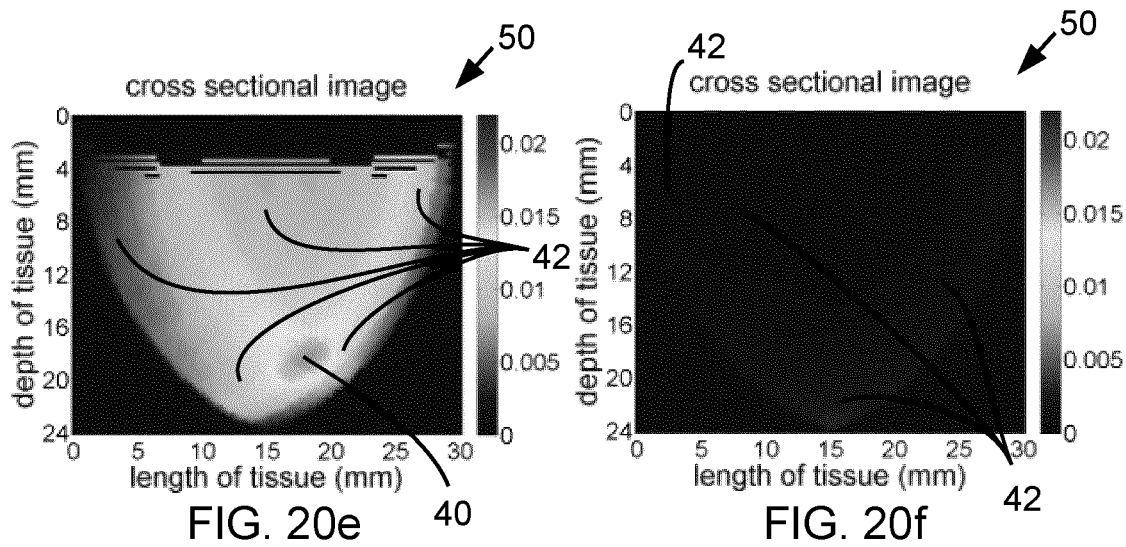
FIG. 20e is a sectional image associated with patient case 10, a wavelength of 800 nm, and the left breast of patient 10.
FIG. 20f is a sectional image associated with patient case 10, a wavelength of 800 nm, and the right breast of patient 10.
Figures 20G, 20H:
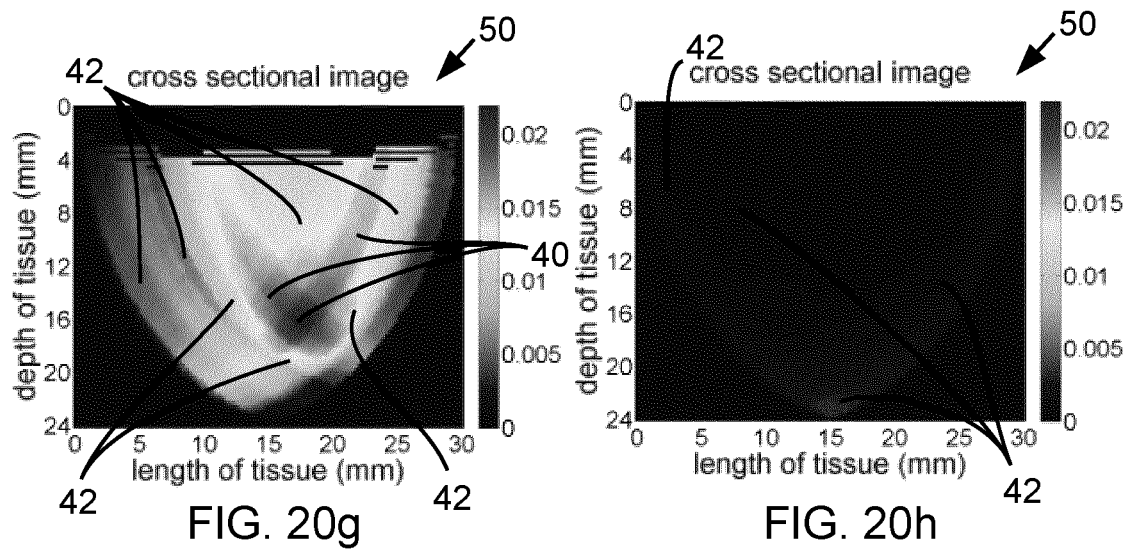
FIG. 20g is a sectional image associated with patient case 10, a wavelength of 850 nm, and the left breast of patient 10.
FIG. 20h is a sectional image associated with patient case 10, a wavelength of 850 nm, and the right breast of patient 10.

Case 6: There was a cancerous lesions in the right breast at 1 o'clock. FIGS. 17a to 17h present that the probe 10 captured the tumor correctly and it is in line with mammography images. There are some reddish areas 40 on the healthy breast which shows a mass in healthy tissue that has a higher absorption coefficient at 800 nm (FIG. 17e) and 850 nm (FIG. 17g). According to FIGS. 17a to 17h, water and fat have higher absorption coefficients than the other two absorbers in breast tissue. Medical advice from the patient's oncologists indicates there was a benign mass which is filled with liquid at the location.

Case 7: There was a cancerous lesions in the right breast between 10 and 11 o'clock. FIGS. 18a to 18h present that the probe 10 captured the tumor correctly and it is in line with mammography images. The DOB-Scan probe's images also show a mass in healthy tissue (FIGS. 18a, 18c, 18e, and 18g) that has a higher absorption coefficient. Medical advice from the patient's oncologists indicates there was a benign mass which filled with liquid at the location.

Case 8: Data collection failed due to technical problem. Thus, images corresponding to this case are not provided in association with the present invention.

Case 9: There was a cancerous lesions in the left breast at 1 o'clock. FIGS. 19a to 19h present that the probe 10 captured the tumor correctly and it is in line with mammography images.

Case 10: There was a cancerous lesions in the left breast at 5 o'clock. FIGS. 20a to 20h present that the probe 10 captured the tumor correctly and it is in line with mammography images.

As shown, the DOB-Scan probe 10 can be used to capture cross-sectional images of the female breast's interior using NIR light sources associated with a linear CCD. The reconstructed preliminary images show that DOB-San probe can identify the cancerous region from the surrounding healthy tissue. The cancerous region is observed in the images due to the higher level of absorption caused by higher levels of vascularization in the cancerous region.

Thus, there is provided a diffuse-optical-spectroscopy system for scanning human tissue. The system includes: (a) a handheld probe operable to emit electromagnetic radiation at one or more wavelengths corresponding to absorption associated with one or more human-tissue constituents, respectively, the handheld probe being operable to detect received electromagnetic radiation at each of the one or more wavelengths; and (b) a processor operable to produce, in response to the received electromagnetic radiation, one or more cross-sectional images of the human tissue respectively associated with the one or more wavelengths.

While embodiments of the invention have been described and illustrated, such embodiments should be considered illustrative of the invention only. The invention may include variants not described or illustrated herein in detail. Thus, the embodiments described and illustrated herein should not be considered to limit the invention as construed in accordance with the accompanying claims.

What is claimed is:

1. A diffuse-optical-spectroscopy system for scanning human tissue, the system comprising:
a handheld probe having at least two emitter sources which emit electromagnetic radiation, the at least two emitter sources are aligned along a first axis and face an outward direction, the at least two emitter sources being encapsulated light-emitting diodes, each of the at least two emitter sources configured to emit electromagnetic radiation at at least four wavelengths corresponding to absorption associated with at least four human-tissue constituents, said at least four human-tissue constituents comprising deoxyhemoglobin, oxyhemoglobin, water and fat;
the handheld probe having one or more sensors, the one or more sensors are aligned along the first axis and face the outward direction, the one or more sensors detect received electromagnetic radiation at each of said one or more visible, near-infrared or infrared wavelengths, said one or more sensors and the at least two emitter sources are located in reflectance geometry and said at least two emitter sources are disposed in spaced relation on either side of said one or more sensors, the one or more sensors is a linear array detector comprising photodiodes or a charge-coupled device; and
a processor operable to produce, in response to said received electromagnetic radiation, one or more cross-sectional images of the human tissue respectively associated with said at least four wavelengths.

2. The system of claim 1 wherein said electromagnetic radiation is continuous wave electromagnetic radiation.

3. The system of claim 1 wherein the one or more sensors is an array photon detector, or an array photodiode.

4. A method of scanning human tissue by diffuse-optical-spectroscopy, the method comprising:
emitting continuous wave electromagnetic radiation through at least two emitter sources at wavelengths between 650 nm and 1100 nm corresponding to absorption associated with one or more human-tissue constituents, respectively, by a handheld probe while being placed in proximity to the human tissue, the at least two emitter sources being encapsulated light-emitting diodes, each of the at least two emitter sources configured to emit electromagnetic radiation at at least four wavelengths corresponding to absorption associated with at least four human-tissue constituents, said at least four human-tissue constituents comprising deoxyhemoglobin, oxyhemoglobin, water and fat;
using one or more sensors to detect received electromagnetic radiation at each of said wavelengths between 650 nm and 1100 nm, said one or more sensors and the at least two emitter sources are aligned in reflectance geometry and said at least two emitter sources are disposed in spaced relation on either side of said one or more sensors, the one or more sensors being one of a linear array detector comprising photodiodes, or a charge-coupled device; and
in response to said received electromagnetic radiation, producing by a processor one or more cross-sectional images of the human tissue respectively associated with said wavelengths between 650 nm and 1100 nm.

5. The method of claim 4 further comprising determining a first absorption coefficient associated with a first emitter source when said first source is emitting first electromagnetic radiation of said electromagnetic radiation, determining a second absorption coefficient associated with a second emitter source when said second source is emitting second electromagnetic radiation of said electromagnetic radiation, and determining a total absorption coefficient at an intersecting location within the human tissue by calculating a superposition value associated with said first absorption coefficient and said second absorption coefficient.

6. The method of claim 4 further comprising measuring an effect of ambient light on a sensor image while all of the at least two emitter sources are turned off.

7. A system for scanning human tissue by diffuse-optical-spectroscopy, the system comprising:
a handheld probe having at least two emitting sources for emitting electromagnetic radiation at wavelengths between 650 nm and 1100 nm, the at least two emitter sources being encapsulated light-emitting diodes, each of the at least two emitter sources configured to emit electromagnetic radiation at at least four wavelengths corresponding to absorption associated with at least four human-tissue constituents, said at least four human-tissue constituents comprising deoxyhemoglobin, on/hemoglobin, water and fat;
the handheld probe having one or more sensors for detecting received electromagnetic radiation at each of said at least four wavelengths, the at least two emitting sources and the one or more sensors being aligned side by side along an axis and facing an outward direction, said at least two emitter sources being disposed along the axis in spaced relation on either side of said one or more sensors, said at least two emitter sources and said one or more sensors being located in reflectance geometry; and
a processor communicating with the handheld probe, the processor producing, in response to said received electromagnetic radiation, one or more cross-sectional images of the human tissue respectively associated with said at least four wavelengths.

\* \* \* \* \*